United States Patent [19]
Kim et al.

[11] Patent Number: 5,688,965
[45] Date of Patent: Nov. 18, 1997

[54] AZABICYCLIC COMPOUNDS USEFUL AS AN INTERMEDIATE FOR THE PREPARATION OF PYIDONE CARBOXYLIC ACID COMPOUNDS AND PROCESS FOR PREPARING THE SAME

[75] Inventors: Choong Sup Kim, Seoul; Jin Woong Kim, Seongnam; Jae Mok Lee, Seoul; Il Hwan Cho; Yong Sik Youn, both of Suwon; Young Jun Shin, Seoul; Ki Ho Lee; Je Hak Kim, both of Suwon; Yong Hwan Jung, Kyonggi-do; Seung Ho An, Seoul, all of Rep. of Korea

[73] Assignee: Cheil Foods & Chemicals, Inc., Seoul, Rep. of Korea

[21] Appl. No.: 592,171

[22] Filed: Jan. 26, 1996

Related U.S. Application Data

[62] Division of Ser. No. 160,821, Dec. 3, 1993, Pat. No. 5,527,910.

[30] Foreign Application Priority Data

Dec. 30, 1992 [KR] Rep. of Korea .................. 92-26696
Jun. 17, 1993 [KR] Rep. of Korea .................. 93-11125

[51] Int. Cl.$^6$ .................. C07D 209/02; C07D 209/04; C07D 209/52
[52] U.S. Cl. .................. 548/452; 514/230.2; 514/300; 514/312; 514/412
[58] Field of Search .................. 548/452; 514/312, 514/300, 230.2, 412

[56] References Cited

U.S. PATENT DOCUMENTS

| | | | |
|---|---|---|---|
| 3,246,006 | 4/1966 | Grubber | 548/452 X |
| 3,246,027 | 4/1966 | Schreyer | 548/452 X |
| 3,252,972 | 5/1966 | Mull | 548/452 X |
| 3,639,390 | 2/1972 | Arya | 548/452 X |
| 3,875,154 | 4/1975 | Rapoport | 546/112 X |
| 4,341,784 | 7/1982 | Matsumoto et al. | 424/256 |
| 4,382,937 | 5/1983 | Matsumoto et al. | 424/256 |
| 4,431,661 | 2/1984 | McKenzie et al. | 548/452 X |
| 4,571,396 | 2/1986 | Hutt et al. | 514/249 |
| 4,962,108 | 10/1990 | Hutt et al. | 514/249 |
| 4,988,709 | 1/1991 | Ogata et al. | 514/314 |
| 5,026,856 | 6/1991 | Yatsunami et al. | 546/156 |
| 5,147,873 | 9/1992 | Kleinman | 546/156 |
| 5,164,402 | 11/1992 | Brighty | 514/300 |
| 5,286,723 | 2/1994 | Hayakawa et al. | 546/156 |
| 5,521,209 | 5/1996 | Steiner et al. | 514/112 |
| 5,527,910 | 6/1996 | Kim et al. | 546/146 |

FOREIGN PATENT DOCUMENTS

| | | | |
|---|---|---|---|
| 2030217 | 5/1991 | Canada | 514/249 |
| 0 200 307 | 11/1986 | European Pat. Off. | 546/156 |
| 0413455 A2 | 2/1991 | European Pat. Off. | 514/314 |
| 0 516 861 | 12/1992 | European Pat. Off. | 546/156 |
| 0 549 857 | 7/1993 | European Pat. Off. | 546/156 |
| 4 120 646 | 12/1992 | Germany | 546/123 |
| 64-56673 | 3/1989 | Japan | 514/314 |
| 91/02526 | 3/1991 | WIPO | 514/249 |

OTHER PUBLICATIONS

Chemical Abstract 66:37500b (1967) Du Pont.
Chemical Abstract 90:5380s. (1978) Thummel et al.
Chemical Abstract 111:153779w. (1990).

*Primary Examiner*—Floyd D. Higel
*Attorney, Agent, or Firm*—Burns, Doane, Swecker & Mathis, L.L.P.

[57] ABSTRACT

Pyridone carboxylic acid compounds and pharmaceutically acceptable salts and physiologically hydrolyzable esters thereof are provided which are represented by the formula:

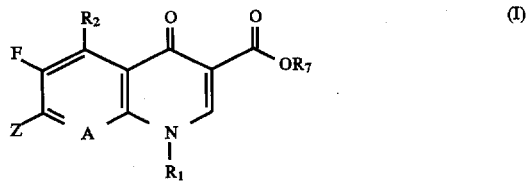

wherein $R_1$ is a lower alkyl, a halogen-substituted lower alkyl, a lower alkenyl, a cycloalkyl, or a substituted- or unsubstituted-phenyl group; $R_2$ is a hydrogen atom, or a lower alkyl or an amino group; A is a nitrogen atom or the group C—X wherein X is a hydrogen or a halogen atom, or an alkoxy group; and Z is a group having the formula:

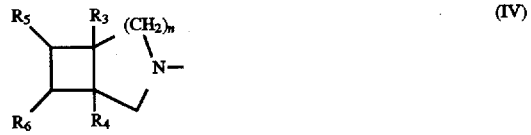

wherein n is 1 or 2; $R_3$ and $R_4$ each represent a hydrogen atom or a lower alkyl group, with proviso that, if n is 2, one of $R_3$ and $R_4$ is a hydrogen atom; $R_5$ and $R_6$ each represent a hydrogen atom, or a hydroxy, a lower alkoxy or an amino group which is unsubstituted or substituted by a lower alkyl group, with proviso that one of $R_5$ and $R_6$ is a hydrogen atom; and $R_7$ is a hydrogen atom or a lower alkyl group. The compounds of the present invention show potent and broad spectrum of antibacterial activities.

11 Claims, No Drawings

AZABICYCLIC COMPOUNDS USEFUL AS AN INTERMEDIATE FOR THE PREPARATION OF PYIDONE CARBOXYLIC ACID COMPOUNDS AND PROCESS FOR PREPARING THE SAME

This application is a divisional application of Ser. No. 08/160,821, filed on Dec. 3, 1993, now U.S. Pat. No. 5,527,910.

TECHNICAL FIELD

The present invention relates to novel pyridone carboxylic acid derivatives, and pharmaceutically acceptable salts and physiologically hydrolyzable esters thereof, and a process for preparing the same. The present invention also relates to a pharmaceutical composition containing one or more of the novel pyridone carboxylic acid derivatives according to the invention as an active ingredient, and a method for treating the bacterial infection comprising administering the same compounds.

BACKGROUND ART

A number of quinolone compounds have been developed and proven successful in commerce, attributing to their potent and broad spectrum of antibacterial activities. Included among such quinolone compounds are Norfloxacin, Enoxacin, Ofloxacin, Ciprofloxacin, and so forth.

In recent years, an extensive investigation has been made to develop a novel structure of pyridone carboxylic acid derivatives which have more potent and broad antibacterial activities. Most of such investigation has been focused onto the development of new substituents at 7-position of the quinolone nucleus.

As prior an references which disclose such derivatives, U.S. Pat. No. 4,988,709, European Patent 0 413 455, and Japanese Laid Open Patent Publication 89-56,673 may be mentioned.

DISCLOSURE OF THE INVENTION

According to the present invention, a novel pyridone carboxylic acid derivative is provided which is represented by the following formula:

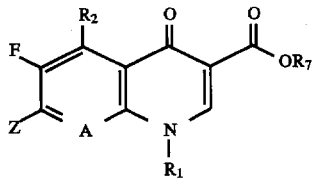

wherein $R_1$ is a lower alkyl, a halogen-substituted lower alkyl, a lower alkenyl, a cycloalkyl, or a substituted- or unsubstituted-phenyl group; $R_2$ is a hydrogen atom, or a lower alkyl or an amino group; A is a nitrogen atom or the group C—X wherein X is a hydrogen or a halogen atom, or an alkoxy group; and Z is a group having the formula:

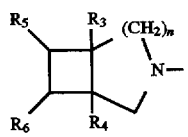

wherein n is 1 or 2; $R_3$ and $R_4$ each represent a hydrogen atom or a lower alkyl group, with provisio that, if n is 2, one of $R_3$ and $R_4$ is a hydrogen atom; $R_5$ and $R_6$ each represent a hydrogen atom, or a hydroxy, a lower alkoxy or an amino group which is unsubstituted or substituted by a lower alkyl group, with provisio that one of $R_5$ and $R_6$ is a hydrogen atom; and $R_7$ is a hydrogen atom or a lower alkyl group; and pharmaceutically acceptable salts thereof and physiologically hydrolyzable esters thereof.

As used herein, the term "halogen" includes chloro, bromo, and fluoro. The term "lower alkyl" may include, for example, methyl, ethyl, propyl, isopropyl, butyl, isobutyl, t-butyl, pentyl, neopentyl, etc. The term "lower alkenyl" may include, for example, vinyl, allyl, 1-propenyl, and isopropenyl. The term "cycloalkyl" includes, for example, cyclopropyl, cyclobutyl, cyclopentyl, and cyclohexyl. The substituent for phenyl group may include, for example, a halogen atom, and a lower alkyl, lower alkoxy, halogeno-lower alkyl, hydroxy, nitro, and amino group. The term "alkoxy" includes, for example, methoxy, ethoxy, propoxy or butoxy group.

The compounds of the formula (I) can be categorized into two groups on the basis of the integer, n.

The compounds of the first group are those wherein n is 1 and can be represented by the following formula:

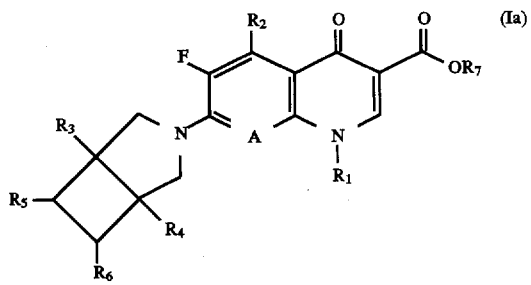

wherein $R_1$, $R_2$, $R_3$, $R_4$, $R_5$, $R_6$, $R_7$ add A have the same meaning as defined above.

Particularly preferred compounds belonging to the first group of the formula (Ia) are as set forth below:

7-([1α,5α,6β]-6-amino-1-methyl-3-azabicyclo[3.2.0]heptane-3-yl)-1-cyclopropyl-6-fluoro-1,4-dihydro-4-oxoquinoline-3-carboxylic acid;

7-([1α,5α,6β]-6-amino-1-methyl-3-azabicyclo[3.2.0]heptane-3-yl)-1-cyclopropyl-6,8-difluoro-1,4-dihydro-4-oxoquinoline-3-carboxylic acid;

5-amino-7-([α,5α,6β]-6-amino-1-methyl-3-azabicyclo[3.2. 0]heptane-3-yl)-1-cyclopropyl-6,8-difluoro-1,4-dihydro-4-oxoquinoline-3-carboxylic acid;

7-([1α,5α,6β]-6-amino-1-methyl-3-azabicyclo[3.2.0]heptane-3-yl)-6,8-difluoro-1-(2,4-difluorophenyl)-1,4-dihydro-4-oxoquinoline-3-carboxylic acid 7-([1α,5α,6β]-6-amino-1-methyl-3-azabicyclo[3.2.0]heptane-3-yl)-1-cyclopropyl-6,8,difluoro-5-methyl-1,4-dihydro-4-oxoquinoline-3-carboxylic acid;

7-([1α,5α,6β]-6-amino-1-methyl-3-azabicyclo[3.2.0]heptane-8-chloro-1-cyclopropyl-6-fluoro-1,4-dihydro-4-oxoquinoline-3-carboxylic acid;

7-([1α,5α,6β]-6-amino-1-methyl-3-azabicyclo[3.2.0]heptane-3-yl)-1-cyclopropyl-6-fluoro-1,4-dihydro-4-oxo-1,8-naphtyridine-3-carboxylic acid;

7-([1α,5α,6β]-6-amino-1-methyl-3-azabicyclo[3.2.0]heptane-3-yl)-1-(2,4-difluorophenyl)-6-fluoro-1,4-dihydro-4-oxo-1,8-naphtyridine-3-carboxylic acid;

7-([1α,5α,6βB]-6-amino-1-methyl-3-azabicyclo[3.2.0]heptane-3-yl)-6-fluoro-1(4-fluorophenyl-1,4-dihydro-4-oxo-1,8-naphtyridine-3-carboxylic acid;

7-([1α,5α,6β]-6-amino-1-methyl-3-azabicyclo[3.2.0]heptane-3-yl)-1-t-butyl-6-fluoro-1,4-dihydro-4-oxo-1,8-naphtyridine-3-carboxylic acid;

7-([1α,5α,6β]-6-amino-1-methyl-3-azabicyclo[3.2.0] heptane-3-yl)-1-(2,4-difluorophenyl)-6-fluoro-5-methyl-1,4-dihydro-4-oxo-1,8-naphtyridine-3-carboxylic acid;

(+)-7-([1α,5α,6β]-6-amino-1-methyl-3-azabicyclo[3.2.0] heptane-3-yl)-1-cyclopropyl-6-fluoro-1,4-dihydro-4-oxo-1,8-naphtyridine-3-carboxylic acid;

(−)-7-([1α,5α,6β]-6-amino-1-methyl-3-azabicyclo[3.2.0] heptane-3-yl)-1-cyclopropyl-6,8-difluoro-1,4-dihydro-4-oxoquinoline-3-carboxylic acid;

(+)-7-([1α,5α,6β]-6-amino-1-methyl-3-azabicyclo[3.2.0] heptane-3-yl)-1-cyclopropyl-6,8-difluoro-1,4-dihydro-4-oxoquinoline-3-carboxylic acid;

1-cyclopropyl-6,8-difluoro-7-([1α,5α,6β]-6-hydroxy-1-methyl-3-azabicyclo[3.2.0]heptane-3-yl)-1,4-dihydro-4-oxoquinoline-3-carboxylic acid;

1-cyclopropyl-6-fluoro-7-([1α,5α,6β]-6-hydroxy-1-methyl-3-azabicyclo[3.2.0]-heptane-3-yl)-1,4-dihydro-4-oxo-1,8-naphtyridine-3-carboxylic acid;

(−)-7-([1α,5α,6β]-6-amino-1-methyl-3-azabicyclo[3.2.0] heptane-3-yl)-1-cyclopropyl-6,8-difluoro-5-methyl-1,4-dihydro-4-oxoquinoline-3-carboxylic acid;

(−)-5-amino-7-([1α,5α,6β]-6-amino-1-methyl-3-azabicyclo[3.2.0.]heptane-3-yl)-1-cyclopropyl-6,8-difluoro-1,4-dihydro-4-oxoquinoline-3-carboxylic acid;

(−)-7-([1α,5α,6β]-6-amino-1-methyl-3-azabicyclo[3.2.0] heptane-3-yl)-1-t-butyl-6-fluoro-1,4-dihydro-4-oxo-1,8-naphtyridine-3-carboxylic acid;

(−)-7-([1α,5α,6β]-6-amino-1-methyl-3-azabicyclo[3.2.0] heptane-3-yl)-8-chloro-1-cyclopropyl-6-fluoro-1,4-dihydro-4-oxoquinoline-3-carboxylic acid;

(−)-7-([1α,5α,6β]-6-amino-1-methyl-3-azabicyclo[3.2.0] heptane-3-yl)-1-(2,4-difluorophenyl)-6-fluoro-1,4-dihydro-4-oxo-1,8-naphtyridine-3-carboxylic acid;

(−)-7-([1α,5α,6β]-6-amino-1-methyl-3-azabicyclo[3.2.0] heptane-3-yl)-1-(4-fluorophenyl)-1,4-dihydro-4-oxo-1,8-naphtyridine-3-carboxylic acid;

7-([1α,5α,6β]-6-amino-5-methyl-3-azabicyclo[3.2.0] heptane-3-yl)-6,8-difluoro-1-cyclopropyl-1,4-dihydro-4-oxoquinoline-3-carboxylic acid;

7-([1α,5α,6β]-6-amino-5-methyl-3-azabicyclo[3.2.0] heptane-3-yl)-6-fluoro-1-4-(fluorophenyl)-1,4-dihydro-4-oxo-1,8-naphtyridine-3-carboxylic acid;

8-chloro-1-cyclopropyl-7-([1α,5α,6β]-6-amino-5-methyl-3-azabicyclo[3.2.0]heptane-3-yl)-6-fluoro-1,4-dihydro-4-oxo-3-quinoline-carboxylic acid;

7-([1α,5α,6β]-6-amino-5-methyl-3-azabicyclo[3.2.0] heptane-3-yl)-1-cyclopropyl-6-fluoro-1,4-dihydro-4-oxo-1,8-naphtyridine-3-carboxylic acid;

1-(2,4-difluorophenyl)-7-([1α,5α,6β]-6-amino-5-methyl-3-azabicyclo[3.2.0]heptane-3-yl)-6-fluoro-1,4-dihydro-4-oxo-1,8-naphtyridine-3-carboxylic acid;

(−)-7-([1α,5α,6β]-6-amino-1-methyl-3-azabicyclo[3.2.0] heptane-3-yl)-1-(2,4-difluorophenyl)-1,4-dihydro-6-fluoro-5-methyl-4-oxo-1,8-naphtyridine-3-carboxylic acid;

1-cyclopropyl-7-([1α,5α,6β]-6-hydroxy-3-azabicyclo [3.2.0]-heptane-3-yl)-6,8-difluoro-1,4-dihydro-4-oxo-3-quinoline-carboxylic acid;

5-amino-1-cyclopropyl-7-([1α,5α,6β]-6-hydroxy-3-azabicyclo[3.2.0]heptane-3-yl)-6,8-difluoro-1,4-dihydro-4-oxo-3-quinoline-carboxylic acid;

1-cyclopropyl-7-([1α,5α,6β]-6-hydroxy-3-azabicyclo [3.2.0]-heptane-3-yl)-6,8-difluoro-1,4-dihydro-5-methyl-4-oxo-3-quinoline-carboxylic acid;

1-cyclopropyl-7-([1α,5α,6β]-6-amino-3-azabicyclo [3.2.0]heptane-3-yl)-6,8-difluoro-1,4-dihydro-5-methyl-4-oxo-3-quinoline-carboxylic acid;

1-cyclopropyl-7-([1α,5α,6β]-6-amino-3-azabicyclo [3.2.0]heptane-3-yl)-6,8-difluoro-1,4-dihydro-4-oxo-3-quinoline-carboxylic acid;

5-amino-1-cyclopropyl-7-([1α,5α,6β]-6-amino-3-azabicyclo[3.2.0]heptane-3-yl)-6,8-difluoro-1,4-dihydro-4-oxo-3-quinoline-carboxylic acid;

1-cyclopropyl-7-([1α,5α,6β]-6-hydroxy-3-azabicyclo [3.2.0]-heptane-3-yl)-6-fluoro-1,4-dihydro-4-oxo-1,8-naphtyridine-3-carboxylic acid;

1-cyclopropyl-7-([1α,5α,6β]-6-amino-3-azabicyclo [3.2.0]heptane-3-yl)-6-fluoro-1,4-dihydro-4-oxo-1,8-naphtyridine-3-carboxylic acid;

7-([1α,5α,6β]-6-amino-3-azabicyclo[3.2.0]heptane-3-yl) -1-(2,4-difluorophenyl)-1,4-dihydro-6-fluoro-4-oxo-1, 8-naphtyridine-3-carboxylic acid;

7-([1α,5α,6β]-6-amino-3-azabicyclo[3.2.0]heptane-3-yl) -1,4-dihydro-6-fluoro-1-(4-fluorophenyl)-4-oxo-1,8-naphtyridine-3-carboxylic acid 7-([1α,5α,6β]-6amino-3-azabicyclo[3.2.0.]heptane-3-yl)-8chloro-1-cyclopropyl-6-fluoro-1,4-dihydro-4-oxo-3-quinoline-carboxylic acid;

7-([1α,5α,6β]-6-amino-3-azabicyclo[3.2.0]heptane-3-yl) -1-(2,4-difluorophenyl)-1,4-dihydro-6-fluoro-5-methyl-4-oxo-1,8-naphtyridine-3-carboxylic acid;;

(−)-7-([1α,5α,6β]-6-amino-3-azabicyclo[3.2.0]heptane-3-yl)-1-(2,4-difluorophenyl)-1,4-dihydro-6-fluoro-4-oxo-1,8-naphtyridine-3-carboxylic acid;

7-([1α,5α,6β]-6-amino-3-azabicyclo-[3.2.0]heptane-3-yl)-1-(t-butyl)-6-fluoro-1,4-dihydro-4-oxo-1,8-naphtyridine-3-carboxylic acid;

(−)-7-([1α,5α,6β]-6-amino-3-azabicyclo[3.2.0]heptane-3-yl)-1-cyclopropyl-1,4-dihydro-6-fluoro-5-methyl-1, 8-naphtyridine-3-carboxylic acid;

7-([1α,5α,6β]-6-amino-1-methyl-3-azabicyclo[3.2.0] heptane-3-yl)-1-cyclopropyl-6-fluoro-8-methoxy-1,4-dihydro-4-oxoquinoline-3-carboxylic acid;

7-([1α,5α,6β]-6-amino-1-methyl-3-azabicyclo[3.2.0] heptane-3-yl)-1-cyclopropyl-6-fluoro-1,4-dihydro-4-oxo-1,8-naphthyridine-3-carboxylic acid;

8-chloro-1-cyclopropyl-6-fluoro-7-([1α,5α,6β]-1-methyl-6-methylamino-3-azabicyclo[3.2.0]heptane-3-yl)-1,4-dihydro-4-oxoquinoline-3-carboxylic acid;

1-cyclopropyl-6,8-difluoro-7-([1α,5α,6β]-1-methyl-6-methylamino-3-azabicyclo[3.2.0]heptane-3-yl)-1,4-dihydro-4-oxoquinoline-3-carboxylic acid;

1-cyclopropyl-6-fluoro-7-([1α,5α,6β]-1-methyl-6-methylamino-3-azabicyclo[3.2.0]-heptane-3-yl)-1,4-dihydro-4-oxo-1,8-naphthyridine-3-carboxylic acid;

7-([1α,5α,6β]-6-amino-3-azabicyclo[3.2.0]heptane-3-yl) -1-cyclopropyl-6-fluoro-1,4-dihydro-4-oxo-1,8-naphthyridine-3-carboxylic acid; and 7-([1α,5α,6β]-6-amino-3-azabicyclo[3.2.0]heptane-3-yl) -1-cyclopropyl-6,8-difluoro-1,4-dihydro-4-oxoquinoline-3-carboxylic acid.

The compounds of the second group are those wherein n is 2 and have the following formula:

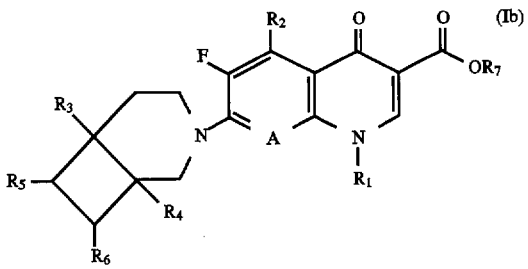

wherein $R_1$, $R_2$, $R_3$, $R_4$, $R_5$, $R_6$, $R_7$ and A have the same meaning as defined above.

Particularly preferred compounds belonging to the second group of the formula (Ib) are as set forth below:

7-([1α,6α,8β]-8-amino-3-azabicyclo[4.2.0]octane-3-yl)-1-cyclopropyl-6-fluoro-1,4-dihydro-4-oxo-1,8-naphthyridine-3-carboxylic acid;

7-([1α,6α,8β]-8-amino-3-azabicyclo[4.2.0]octane-3-yl)-1-(2,4-difluorophenyl)-1,4-dihydro-4-oxo-1,8-naphthyridine-3-carboxylic acid;

7-([1α,6α,8β]-8-amino-3-azabicyclo[4.2.0]octane-3-yl)-1-(4-fluorophenyl)-1,4-dihydro-4-oxo-1,8-naphthyridine-3-carboxylic acid;

7-([1α,6α,8β]-8-amino-3-azabicyclo[4.2.0]octane-3-yl)-1-cyclopropyl-6,8-difluoro-4-oxoquinoline-3-carboxylic acid;

7-([1α,6α,8β]-8-amino-3-azabicyclo[4.2.0]octane-4-yl)8-chloro-1-cyclopropyl-6-fluoro-1,4-dihydro-4-oxoquinoline-3-carboxylic acid;

7-([1α,6α,8β]-8-amino-3-azabicyclo[4.2.0]octane-4-yl)-5-amino-1-cyclopropyl-6,8-difluoro-1,4-dihydro-4-oxoquinoline-3-carboxylic acid;

7-([1α,6α,8β]-8-amino-3-azabicyclo[4.2.0]octane-3-yl)-1-cyclopropyl-6,-fluoro-1,4-dihydro-4-oxoquinoline-3-carboxylic acid;

7-([1α,6α,8β]-8-amino-3-azabicyclo[4.2.0]octane-3-yl)-5-methyl-1-cyclopropyl-6,8-difluoro-1,4-dihydro-4-oxoquinoline-3-carboxylic acid;

7-([1α,6α,8β]-8-amino-3-azabicyclo[4.2.0.]octane-3-yl)-6-fluoro-1-tert.-butyl-1,4-dihydro-4-oxo-1,8-naphthyridine-3-carboxylic acid;

7-([1α,6α,8β]-8-amino-3-azabicyclo[4.2.0]octane-3-yl)-8-chloro-6-fluoro-5-methyl-1-cyclopropyl-1,4-dihydro-4-oxoquinoline-3-carboxylic acid;

7-([1α,6α,8β]-8-amino-3-azabicyclo[4.2.0]octane-3-yl)-1-cyclopropyl-5-methyl-6-fluoro-1,4-dihydro-4-oxoquinoline-3-carboxylic acid;

(+)-7-([1α,6α,8β]-8-amino-3-azabicyclo[4.2.0]octane-3-yl)-1-cyclopropyl-6-fluoro-1,4-dihydro-4-oxo-1,8-naphthyridine-3-carboxylic acid;

(−)-7-([1α,6α,8β]-8-amino-3-azabicyclo[4.2.0]octane-3-yl)-1-cyclopropyl-6-fluoro-1,4-dihydro-4-oxo-1,8-naphthyridine-3-carboxylic acid;

(−)-7-([1α,6α,8β]-8-amino-3-azabicyclo[4.2.0]octane-3-yl)-1-cyclopropyl-6,8-difluoro-1,4-dihydro-4-oxoquinoline-3-carboxylic acid;

(+)-7-([1α,6α,8β]-8-amino-3-azabicyclo[4.2.0]octane-3-yl)-1-cyclopropyl-6,8-difluoro-1,4-dihydro-4-oxoquinoline-3-carboxylic acid;

7-([1α,6α,8β]-8-amino-3-azabicyclo[4.2.0]octane-3-yl)-1-cyclopropyl-6-fluoro-8-methoxy-1,4-dihydro-4-oxoquinoline-3-carboxylic acid;

7-([1α,6α,8β]-8-amino-6-methyl-3-azabicyclo[4.2.0]octane-3-yl)-1-cyclopropyl-6-fluoro-1,4-dihydro-4-oxo-1,8-naphthyridine-3-carboxylic acid (hydrochloride);

7-([1α,6α,8β]-8-amino-6-methyl-3-azabicyclo[4.2.0]octane-3-yl)-1-cyclopropyl-6-fluoro-1,4-dihydro-4-oxo-1,8-naphthyridine-3-carboxylic acid (hydrochloride); and 7-([1α,6α,8β]-8-amino-6-methyl-3-azabicyclo[4.2.0]octane-3-yl)-1-cyclopropyl-6,8-difluoro-1,4-dihydro-4-oxoquinoline-3-carboxylic acid.

The compounds of the formula (I) may be converted to pharmaceutically acceptable, non-toxic salts thereof according to conventional methods. Included among the non-toxic salts are inorganic acid addition salts, for example, hydrochloride, sulfate, phosphate, etc.; organic acid addition salts, for example, acetate, pyruvate, oxalate, succinate, methanesulphonate, maleate, malonate, gluconate, etc.; salts with an acidic amino acid, for example, those with asparaginic acid, glutamic acid, etc.; metal salts, for example, salts with sodium, potassium, calcium, magnesium, zinc, silver, etc.; those with an organic base, for example, those with dimethylamine, triethylamine, dicyclohexylamine, benzylamine, etc.; and salts with a basic amino acid, for example, those with lysine, arginine, etc.

The esters of the compounds of the formula (I) may be in any form of known esters which can be physiologically hydrolyzed or easily converted into the compounds of the formula (I). A representative example includes lower alkyl esters, for example, methyl ester, ethyl ester, etc., acetoxymethyl ester, pivaloyloxymethyl ester, ethoxycarbonylethyl ester, choline ester, aminoethyl esters such as 1-piperidinylethyl ester, dimethylamino-ethyl ester, etc., 5-indinyl ester, or phthalidinyl ester, etc.

The compounds according to the invention may be obtained in the form of hydrates by means of conventional methods. Thus, it should also be understood that such hydrates fall within the scope of the invention.

In addition, the compounds of the invention may be in the form of optical isomers owing to the presence of an asymmetric carbon atom at 7-position. The present invention encompasses such optically active compounds of the formula (I).

In another aspect, the invention provides a process for preparing the novel compounds of formula (I) comprising the steps of:

reacting a compound of the formula:

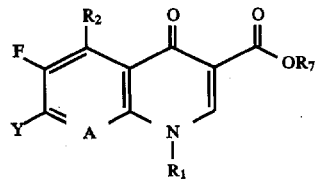

wherein $R_1$ is a lower alkyl, a halogen-substituted lower alkyl, a lower alkenyl, a cycloalkyl, or a substituted- or unsubstituted-phenyl group; $R_2$ is a hydrogen atom, or a lower alkyl or an amino group; A is a nitrogen atom or the group C—X, wherein X is a hydrogen atom, a halogen atom or an alkoxy group; Y is a halogen atom; $R_7$ is a hydrogen atom or a lower alkyl group;

with a compound of formula:

Z—H  (III)

wherein Z is a group having the formula:

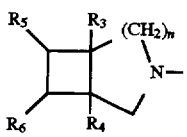

(IV)

wherein n is 1 or 2; $R_3$ and $R_4$ each represent a hydrogen atom or a lower alkyl group, with provisio that, if n is 2, one of $R_3$ and $R_4$ is a hydrogen atom; $R_5$ and $R_6$ each represent a hydrogen atom, or a hydroxy, a lower alkoxy, or an amino group which is unsubstituted or substituted by a lower alkyl group, with provisio that one of $R_5$ and $R_6$ is a hydrogen atom; and if necessary, hydrolyzing the compound of the formula (I) in which $R_7$ is a lower alkyl group.

The reaction of the starting compounds of the formulae (II) and (III) is preferably performed in the presence of an inert organic solvent, for example, alcohols such as ethanol; ethers such as dioxane, tetrahydrofuran or 1,2-dimethoxyethane; aromatic hydrocarbons such as benzene, toluene or xylene; acetonitriles; dimethylformamide; dimethylsulfoxide; pyridine; or water. The reaction is carried out at 0° to 200° C. for 10 min. to 24 hrs.

The compounds of the formula (III) may be used in an amount equivalent to or in excess of the compounds of the formula (II) in the presence of an acid receptor. In this reaction, the compounds of the formula (II) may act as an acid receptor. Thus, when using the compounds of the formula (III) in an excessive amount, it is not necessary to use an acid receptor additionally.

The acid receptors which can be used in the invention are known in the art. Included among such acid receptors are, for example, hydroxides such as sodium hydroxide or potassium hydroxide; carbonates such as sodium carbonate or potassium carbonate; bicarbonates such as sodium bicarbonate or potassium bicarbonate; or an organic base such as triethylamine, dimethylaniline, N,N-diisopropylethylamine or 1,8-diazabicyclo[5.4.0]undec-7-ene (DBU).

In the above reaction, the starting compounds (III) can be used as they stand or with the 1-position amine group protected. The amine protecting group should be readily removable after completing the reaction by using a known method without causing adverse effect on the resulting compounds. Such protecting groups have been well known in peptides, amino acids, hexane or β-lactam chemistry. Preferred examples include hydrolyzable groups such as acetyl, trifluoroacetyl or ethoxycarbonyl, or benzyl group, and so forth.

The compounds of the formula (II) may be prepared according to the methods known in the art. See, *J. Med. Chem.* (1988), 31, p. 503; *J. Org. Chem.* (1981), 46, p. 846; European Patent 0 132 845(1985); U.S. Pat. No. 4,826,987 (1987); European Patent 0 271 275 (1987); Japanese Patent (Hei) 01-268,662; Japanese Patent (Sho) 64-16,746; *J. Heterocyclic Chem.* (1990), 27, p. 1609; *J. Heterocyclic Chem.* (1991), 28, p. 541.

The compounds of the formula (III) used in the present invention are novel and can be prepared by a known method.

For example, 6-amino-1-methyl-3-azabicyclo[3.2.0] heptane can be prepared according to the following reaction scheme A:

Reaction Scheme A

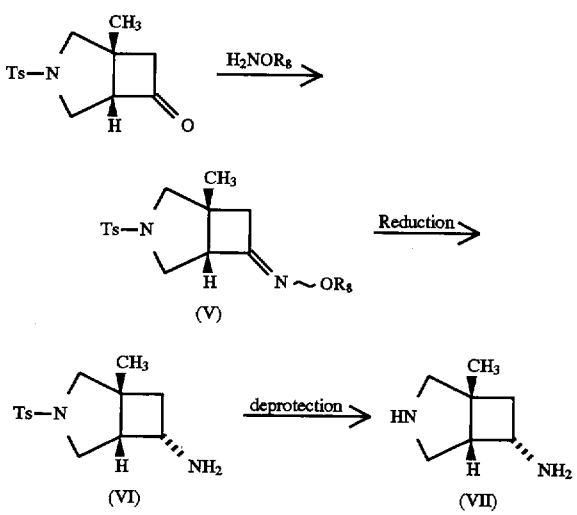

wherein $R_1$ represents a hydrogen atom or methyl group.

In the above reaction scheme, N-p-toluenesulfonyl-1-methyl-6-oxo-3-azabicyclo[3.2.0]heptane is condensed with methoxyamine or hydroxyamine hydrochloride in the presence of a base to give a methoxyimine or hydroxyimine compound of the formula (V). The starting compound is known in the art. See, *Heterocycles* (1989), 25, p.29. The resulting compound is then reduced with an appropriate reducing agent to give an amino compound of the formula (VI). Deprotection of the amino compound in the presence of an acid provides [1α,5α,6β]-6-amino-1-methyl-3-azabicyclo[3.2.0.]heptane of the formula (VII) in racemic forms.

The amino compound of the formula (VI) may be condensed with N-p-toluenesulphonyl-L-phenylalanine to give an amide compound of the formula (VIII) or (IX) in racemic forms. The resulting amide compound is then resolved through column chromatography or recrystalization into each of optically active diastereomers thereof, which is then hydrolyzed with an acid to give an optical isomers.

The reaction involved in the above optical resolution is illustrated in the following scheme B:

Reaction Scheme B

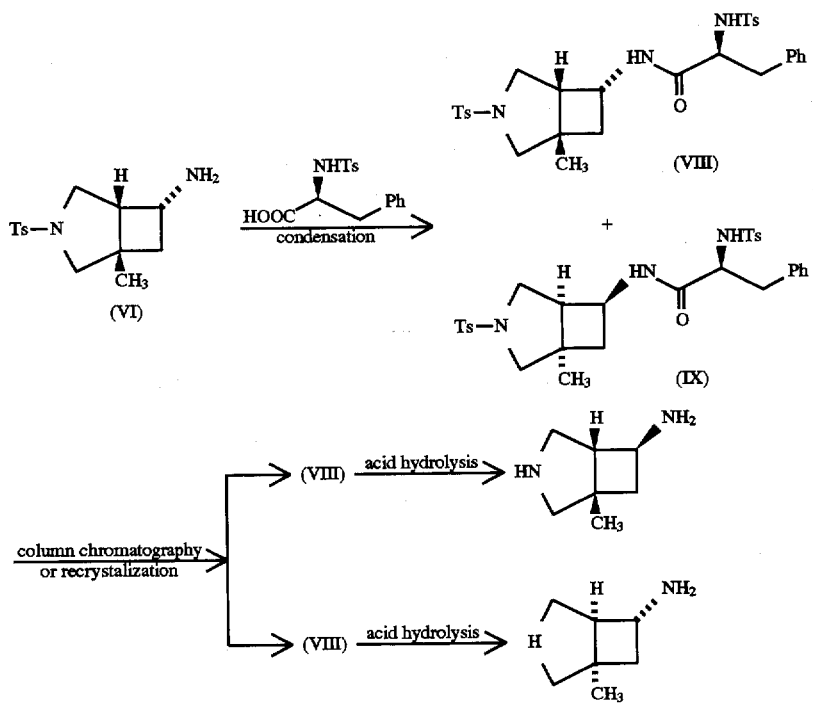

Meanwhile, [1α,5α,6β]-6-hydroxy-1-methyl-3-azabicyclo[3.2.0]heptane of the formula (XI) can be obtained according to a known method as set forth in the following reaction scheme C, in which N-p-toluenesulfonyl-1-methyl-6-oxo-3-azabicyclo[3.2.0]heptane is reduced with a reducing agent to give an alcoholic compound of the formula (X), followed by subjecting to conventional acid hydrolysis.

Reaction Scheme C

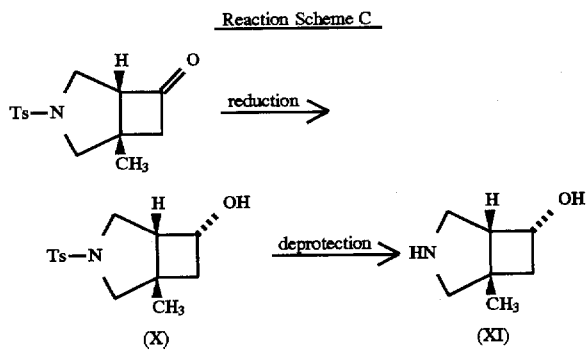

[1α,6α,8β]-8-Amino-3-azabicyclo[4.2.0]octane can also be prepared in the same manner as in the reaction scheme A. More specifically, N-p-toluenesulfonyl-8-oxo-3-azabicyclo[4.2.0]octane is condensed with methoxyamine or hydroxyamine hydrochloride in the presence of a base to give a corresponding methoxyimine or hydroxyimine compound. The starting compound is known in the art. See, Heterocycles (1989), 25, p.29. The resulting compound is then reduced with an appropriate reducing agent to give an amino compound. Deprotection of the amino compound in the presence of an acid provides [1α,5α,6β]-8-amino-3-azabicyclo[4.2.0]octane in racemic forms.

The resulting amino compound in racemic form may also be resolved into its optical isomer using the same procedures as in the reaction scheme B.

The compounds of the formula (I) obtained in the form of esters may be converted into corresponding free acids by hydrolyzing the ester moiety according to the conventional processes. If necessary, the compounds of the formula (I) in the form of free acids may be converted into corresponding esters by conventional methods.

The resulting compounds of the invention are isolated and purified by using conventional methods known in the art. Depending on the conditions for isolation and purification, the compounds of the formula (I) can be obtained in the form of either a salt or a free acid. These two forms of compounds can be interconverted from one to another according to conventional methods.

The compounds of the formula (I), as well as non-toxic salts and physiologically hydrolyzable esters thereof, are useful as antibiotics for treating infectious diseases in mammal caused by bacteria. The compounds of the formula (I) may also be used for the treatment of fish diseases and plant diseases, or in the foodstuffs as a preservant.

When the compounds of the invention are to be used for treating human diseases, the specific dosage depends on various factors, for example, the age and body weight of the individual patients in need of such treatment, the nature and severeness of the diseases, and the administration routes. However, the preferred dosage range which may be presented in an unit dose or multidose is from 5 mg to 5 g/kg of body weight per day. The compounds of the invention can be administered by way of an oral or parenteral route.

In another aspect, the invention also provides a pharmaceutical composition which contains, as an active ingredient, one or more of the compounds of the formula (I), or pharmaceutically acceptable salts or physiologically hydrolyzable esters thereof, in admixture or association with pharmaceutically acceptable carriers which do not react with the active ingredient. The pharmaceutical composition according to the invention may be in various forms such as tablets, oral or injectable solutions, capsules, granules, microgranules, powders, syrups, ointments, etc.

The pharmaceutically acceptable carrier which can be used in the present invention is known in the art. As a carrier for an oral administration, starch, mannitol, crystalline cellulose, CMC—Na, water, ethanol, and so forth may be mentioned. Carriers for an injectable solution include, for example, water, a physiological saline solution, a glucose solution, a sap solution, and the like.

PREFERRED EMBODIMENTS OF THE INVENTION

The present invention will be described in greater detail by way of the following examples. The examples are presented for illustration purpose only and should not be construed as limiting the invention which is properly delineated in the claims.

Preparation 1: [1α,5α]-6-Methoxyimino-1-methyl-3-(p-toluenesulphonyl)-3-azabicyclo[3.2.0]heptane A mixture of 40.0 g of [1α,5α]-1-methyl-6-oxo-3-(p-toluenesulphonyl)-3-azabicyclo[3.2.0]heptane, 14.35 g of methoxyamine hydrochloride and 400 ml of pyridine was stirred at room temperature for 2 hours. The resulting mixture was concentrated under reduced pressure. The residue was dissolved in 500 ml of ethyl acetate. The resulting solution was washed twice with 200 ml of an aqueous 5% hydrochloric acid solution and once with 200 ml of a saturated sodium chloride solution, and then dried over anhydrous magnesium sulfate. The solids formed were filtered off under reduced pressure. The filtrate was concentrated under reduced pressure to give 43.0 g of the titled compound as a yellowish-brown oil (yield: 98%).

$^1$H-NMR(CDCl$_3$) δ:7.7(2H, d, J=8.28 Hz), 7.3(2H, d, J=9.6 Hz), 3.84(0.6H,s), 3.81(0.4H, s), m), 2.4(3H, s), 1.3(3H, s).

Preparation 2: [1α,5α,6β]-6-Amino-1-methyl-3-(p-toluenesulphonyl)-3-azabicyclo[3.2.0]-heptane To a suspension of 27.0 g of NaBH$_4$ in 150 ml of tetrahydrofuran (THF) was added a solution of 55.0 ml of trifluoroacetic acid (TFA) in 150 ml of THF at room temperature for 2 hours. Separately, 43.0 g of the titled compound from Preparation 1 was dissolved in 200 ml of THF. The resulting solution was then added to the solution previously prepared at room temperature for 2 hours. The reaction mixture was stirred at room temperature for 3 hours, to which 50 ml of water and 30 ml of an aqueous 40% sodium hydroxide solution were added. The mixture was heated under reflux for 5 hours. The resulting solution was concentrated under reduced pressure to remove THF, and extracted three times with 200 ml of dichloromethane. The organic layer was washed with 200 ml of a saturated aqueous sodium chloride solution, and then dried over anhydrous magnesium sulfate. The solids formed were filtered off under reduced pressure. The filtrate was concentrated under reduced pressure to give 39.0 g of the titled compound as a yellowish-brown oil (yield: 98%).

$^1$H-NMR(CDCl$_3$) δ:7.7-7.1(4H, m), 3.4-2.0(10H, m), 2.3(3H, s), 1.3(3H, s).

Preparation 3: [1α,5α,6β]-6-Amino-1-methyl-3-azabicyclo[3.2.0]heptane

A mixture of 5.0 g of the titled compound from Preparation 2 and 30 ml of an aqueous 48% hydrobromic acid solution was heated under reflux for 5 hours. The reaction solution was concentrated under reduced pressure. The residue was dissolved in 5 ml of water, to which 3 ml of an aqueous 40% sodium hydroxide solution was added. The mixture was extracted three times with 100 ml of chloroform. The organic layer was dried with anhydrous sodium sulfate. The solids formed were filtered off under reduced pressure. The filtrate was concentrated under reduced pressure to give 1.8 g of the rifled compound as a pale-yellow oil (yield: 80%).

$^1$H-NMR(CDCl$_3$) δ: 3.5-2.5(10H, m), 1.3-1.1(1H, m), 1.26(3H, s).

Preparation 4: [1α,5α,6β]-6-Hydroxy-1-methyl-3-(p-toluenesulphonyl)-3-azabicyclo[3.2.0]heptane To a solution of 2.00 g of [1α,5α]-1-methyl-6-oxo-3-(p-toluenesulphonyl)-3-azabicyclo[3.2.0]heptane in 30 ml of ethanol was added 0.19 g of NaBH$_4$. The resulting mixture was stirred at room temperature for an hour, and concentrated under reduced pressure. The residue was dissolved in 20 ml of water, acidified with an aqueous 5% hydrochloric acid solution, and then stirred at room temperature for an hour. The solids thus formed were collected by filtration under reduced pressure, washed with water, and dried to give 1.82 g of the titled compound as pale-yellow solids (yield: 91%).

$^1$H-NMR(CDCl$_3$) δ: 7.6–7.1(4H, m), 4.3–3.9(1H, m), 3.7–1.8(8H, m), 2.36 (3H, s), 1.13(3H, s).

Preparation 5: [1α,5α,6β]-6-Hydroxy-1-methyl-3-azabicyclo[3.2.0]heptane

A mixture of 1.50 g of the titled compound from Preparation 4 and 20 ml of an aqueous 48% hydrobromic acid solution was heated under reflux for 5 hours, and concentrated under reduced pressure. To the residue, 5 ml of water and 3 ml of an aqueous 40% sodium hydroxide solution were added. The resulting mixture was extracted three times with 50 ml of chloroform. The organic layer was dried over anhydrous sodium sulfate. The solids formed were filtered off under reduced pressure. The filtrate was concentrated under reduced pressure to give 0.54 g of the titled compound as a pale-yellow oil (yield: 80%).

$^1$H-NMR(CDCl$_3$) δ: 4.5–3.9(1H, m), 3.6–1.7(9H, m), 1.2(3H, s).

Preparation 6: (−)-[1α,5α,6β]-6-Amino-1-methyl-3-azabicyclo[3.2.0]heptane and (+)-[1α,5α,6β]-6-amino-1-methyl-3-azabicyclo[3.2.0]heptane (1) To a solution of 1.20 g of [1α,5α,6β]-6-amino-1-methyl-3-(p-toluenesulphonyl)- 3-azabicyclo[3.2.0]heptane and 1.51 g of N-(p-toluenesulphonyl)-L-phenylalanine in 30 ml of dimethylformamide were added 0.78 ml of diethyl cyanophosphate and 1.20 ml of triethylamine. The mixture was stirred at room temperature for 5 hours. The reaction mixture was diluted with 200 ml of ethyl acetate, washed twice with 100 ml of an aqueous 5% hydrochloric acid solution, twice with 100 ml of a saturated sodium hydrogen carbonate solution, twice with 100 ml of water and once with 100 ml of a saturated sodium chloride solution, and then dried over anhydrous magnesium sulfate. After filtering the solids off under reduced pressure, the filtrate was concentrated under reduced pressure. To the residue was added 20 ml of ethanol. The resulting solution was stirred at room temperature for an hour and filtered under reduced pressure to give 0.67 g of white solids. The filtrate was concentrated under reduced pressure, and subject to chromatography using silica gel to give 1.00 g of a colorless oil.

(2) A solution of 0.67 g of the white solid from (1) above in 20 ml of an aqueous 48% hydrobromic acid solution was heated under reflux for 8 hours, and concentrated under reduced pressure. The residue was dissolved in 5 ml of water. To the solution, 2 ml of an aqueous 40% sodium hydroxide solution was added. The resulting mixture was extracted three times with 30 ml of chloroform. The organic layers were combined together, and dried over anhydrous sodium sulfate. The solids were filtered off under reduced pressure. The filtrate was concentrated under reduced pressure to give 0.13 g of (−)-[1α,5α,6β]-6-amino-1-methyl-3-azabicyclo[3.2.0]heptane as a pale-yellow oil (yield: 48%).

[α]$_D^{20}$−15.2 (C=1.0, MeOH).

$^1$H-NMR(CDCl$_3$) δ: 3.5–2.5(10H, m), 1.3–1. l(1H, m), 1.26(3H, s).

(3) A solution of 1.00 g of the oil from (1) above and 20 ml of an aqueous 48% hydrobromic acid solution was treated in the same manner as in (2) above to give 0.19 g of (+)-[1α,5α,6β]-amino-1-methyl-3-azabicyclo[3.2.0]heptane as a pale-yellow oil (yield: 70%).

[α]$_D^{20}$ 15.0(C=1.0, MeOH).
$^1$H-NMR(CDCl$_3$) δ: 3.5–2.5(10H, m), 1.3–1.1(1H, m), 1.26(3H, s).

Preparation 7: [1α,5α]-6-Methoxyimino-3-(p-toluenesulphonyl)-3-azabicyclo[3.2.0]heptane A mixture of 35.5 g of [1α,5α]-6-oxo-3-(p-toluenesulphonyl)-3-azabicyclo[3.2.0]-heptane, 15.0 g of methoxyamine hydrochloride, and 500 ml of pyridine was stirred at room temperature for 3 hours, and concentrated under reduced pressure. The residue was dissolved in 500 ml of ethyl acetate, washed twice with 200 ml of an aqueous 5% hydrochloric acid solution and once with 200 ml of a saturated aqueous sodium chloride solution, and then dried over anhydrous magnesium sulfate. The solids thus formed were filtered off under reduced pressure. The filtrate was concentrated under reduced pressure to give 39.0 g of the titled compound as a yellowish-brown oil (yield: 99%).

$^1$H-NMR(CDCl$_3$) δ: 7.7–7.2(4H, m), 3.73(3H, d, J=1.2Hz), 3.60–3.35(3H, m), 3.05–2.4(5H, m), 2.35(3H,s).

Preparation 8: [1α,5α,6β]-6-Amino-3-(p-toluenesulphonyl)-3-azabicyclo[3.2.0]heptane To a suspension of 20.0 g of NaBH$_4$ in 150 ml of THF was added 37.0 ml of trifluoroacetic acid (TFA) in 200 ml of THF at room temperature for 2 hours. To this mixture was added 25.0 g of the titled compound from Preparation 7 in 200 ml of THF at room temperature for 2 hours. The reaction solution was stirred at room temperature for 3 hours. After adding 50 ml of water and 50 ml of an aqueous 40% sodium hydroxide solution, the mixture was heated under reflux for 5 hours. The resulting solution was concentrated under reduced pressure to remove THF, and extracted three times with 200 ml of dichloromethane. The organic layer was washed with 200 ml of a saturated aqueous sodium chloride solution, and then dried over anhydrous magnesium sulfate. The solids thus formed were filtered off under reduced pressure. The filtrate was concentrated under reduced pressure to give 21.5 g of the titled compound as a yellowish-brown oil (yield: 95%).

$^1$H-NMR(CDCl$_3$) δ: 7.7–7.2(4H, m), 3.5–2.0(11H, m), 2.35(3H, s).

Preparation 9: [1α,5α,6β]-6-Amino-3-azabicyclo[3.2.0]heptane

A mixture of 7.0 g of the titled compound from Preparation 8 and 50 ml of an aqueous 48% hydrobromic acid solution was heated under reflux for 5 hours, and concentrated under reduced pressure. The residue was dissolved in 5 ml of water, to which was added 3 ml of an aqueous 40% sodium hydroxide solution. The reaction solution was extracted three times with 100 ml of chloroform. The organic layer was dried with anhydrous sodium sulfate. The solids were filtered off under reduced pressure. The filtrate was concentrated under reduced pressure to give 2.1 g of the titled compound as a pale yellow-oil (yield: 71.3%).

$^1$H-NMR(CDCl$_3$) δ: 3.5–2.4(11H, m), 1.3–1.1(1H, m).

Preparation 10: [1α,5α,6β]-6-Hydroxy-3-(p-toluenesulphonyl)-3-azabicyclo[3.2.0]heptane The same procedure as in Preparation 4, except for using 1.90 g of [1α,5α]-6-oxo-3-(p-toluenesulphonyl)-azabicyclo[3.2.0]heptane in place of [1α,5α]-1-methyl-6-oxo-3-(p-toluenesulphonyl)-3-azabicyclo[3.2.0]heptane, was repeated to give 1.76 g of the titled compound (yield: 92%).

$^1$H-NMR(CDCl$_3$) δ: 7.7–7.2(4H, m), 4.3–3.8(1H, m), 3.6–1.8(9H,m), 2.4(3H,s).

Preparation 11: [1α,5α,6β]-6-Hydroxy-3-azabicyclo[3.2.0]heptane

The same procedure as in Preparation 5 was repeated using 1.43 g of the titled compound obtained in Preparation 10 to give 0.54 g of the titled compound (yield: 90%).

$^1$H-NMR(CDCl$_3$) δ: 4.5–4.0(1H, m), 3.6–1.6(10H, m).

Preparation 12: [1α,5α]-6-Methoxyimino-5-methyl-3-(p-toluenesulphonyl)-3-azabicyclo[3.2.0]heptane A mixture of 20.0 g of [1α,5α]-5-methyl-6-oxo-3-(p-toluenesulphonyl)-3-azabicyclo[3.2.0]heptane, 7.4 g of methoxyamine hydrochloride, and 300 ml of pyridine was stirred at room temperature for 3 hours. The reaction mixture was treated in the same manner as in Preparation 7 to give 18.9 g of the titled compound as a yellowish-brown oil (yield: 85.6%).

$^1$H-NMR(CDCl$_3$) δ: 7.8–7.2(4H, m), 3.85(3H, s), 4.0–2.5 (7H, m), 2.45(3H, s), 1.3(3H, s).

Preparation 13: [1α,5α,6β]-6-amino-5-methyl-3-(p-toluenesulphonyl)-3-azabicyclo[3.2.0]heptane The same procedure as in Preparation 8 was repeated using 18.9 g of the titled compound obtained in Preparation 12 to give 14.6 g of the titled compound (yield: 85%).

$^1$H-NMR(CDCl$_3$) δ: 7.8–7.2(4H, m), 3.5–2. 1(10H, m), 2.4(3H, s), 1.35(3H,s).

Preparation 14: [1α,5α,6β]-6-Amino-5-methyl-3-azabicyclo[3.2.0]heptane

The same procedure as in Preparation 9 was repeated using 11.0 g of the titled compound obtained in Preparation 13 to give 3.3 g of the titled compound (yield: 67%).

$^1$H-NMR(CDCl$_3$) δ: 3.7–2.7(10H, m), 1.5–1.2(1H, m), 1.3(3H, s).

Preparation 15: (−)[1α,5α,6β]-6-Amino-3-azabicyclo[3.2.0]heptane and (+)-[1α,5α,6β]-6-amino-3-azabicyclo[3.2.0]heptane (1) To a solution of 1.15 g of [1α,5α,6β]-6-amino-3-(p-toluenesulphonyl)-3-azabicyclo[3.2.0]heptane and 1.51 g of N-(p-toluenesulphonyl)-L-phenylalanine in 30 ml of dimethylformamide were added 0.78 ml of diethyl cyanophosphonate and 1.20 ml of triethylamine. The mixture was stirred at room temperature for 5 hours. The reaction mixture was diluted with 200 ml of ethyl acetate, and washed twice with 100 ml of an aqueous 5% hydrochloric acid solution, twice with 100 ml of a saturated aqueous sodium hydrogen carbonate solution, twice with 100 ml of water, and once with 100 ml of a saturated aqueous sodium chloride solution, and then dried over anhydrous magnesium sulfate. After filtering the solids off under reduced pressure, the filtrate was concentrated under reduced pressure. To the residue, 20 ml of ethanol was added. The resulting solution was stirred at room temperature for an hour and filtered under reduced pressure to give 0.67 g of white solids. The filtrate was concentrated under reduced pressure, and subject to chromatography over silica gel to give 1.00 g of a colorless oil.

(2) A solution of 0.67 g of the white solids from (1) above in 20 ml of an aqueous 48% hydrobromic acid solution was heated under reflux for 8 hours and concentrated under reduced pressure. The residue was dissolved in 5 ml of water, to which 2 ml of an aqueous 40% sodium hydroxide solution was added. The resulting mixture was extracted three times with 30 ml of chloroform. The organic layers were combined together, and dried over anhydrous sodium sulfate. The solids were filtered off under reduced pressure. The filtrate was concentrated under reduced pressure to give 0.13 g of (−)-[1α,5α,6β]-6-amino-3-azabicyclo[3.2.0]heptane as a pale-yellow oil (yield: 48% ).

[α]$_D^{20}$−14.0(C=1.0, MeOH).
$^1$H-NMR(CDCl$_3$) δ: 3.5–1.5(12H, m).

(3) A solution of 1.00 g of the oil obtained in (1) above and 20 ml of an aqueous 48% hydrobromic acid solution was treated in the same manner as in (2) above to give 0.19 g of (+)-[1α,5α,6β]-6-amino-3-azabicyclo[3.2.0]heptane as a pale-yellow oil (yield: 70%).

[α]$_D^{20}$+13.8(C=1.0, MeOH).
$^1$H-NMR(CDCl$_3$) δ: 3.48–1.52(12H, m).

Preparation 16: [1α,5α,6α]-1-Methyl-6-(phthalimido-1-yl)-3-(p-toluenesulphonyl)-3azabicyclo[3.2.0]heptane To a solution of 7.00 g of [1α,5α,6β]-6-hydroxy-1-methyl-3-(p-toluenesulphonyl)-3-azabicyclo[3.2.0]heptane, 7.35 g of phthalimide, and 13.09 g of triphenylphosphine in 70 ml of THF was added 8.67 g of diethyl azodicarboxylate. The resulting solution was stirred at room temperature for 5 hours and concentrated under reduced pressure. The residue was dissolved in 300 ml of ethyl acetate, and washed three times with 100 ml of an aqueous 5% sodium hydroxide solution, once with 100 ml of an aqueous 5% hydrochloric acid solution, and once with 100 ml of a saturated aqueous sodium chloride solution. The organic layer was dried over anhydrous magnesium sulfate and concentrated under reduced pressure. To the residue was added a small amount of methanol. The resulting mixture was stirred at room temperature for an hour. The solids thus formed were collected by filtration, and then dried to give 3.50 g of the titled compound as pale-yellow solids (yield: 34%).

m.p.: 180°–184° C.

$^1$H-NMR(CDCl$_3$) δ: 7.9–7.6(6H, m), 7.35 (2H, d, J=8.62Hz), 4.7–4.3(1H, m), 3.6–2.3(7H, m), 2.45(3H, s), 1.38(3H, s).

Preparation 17: [1α,5α,6α]-6-Amino-1-methyl-3-(p-toluenesulphonyl)-3-azabicyclo[3.2.0]heptane A solution of 0.70 g of [1α,5α,6α]-1-methyl-6-(phthalimido-1-yl)-3-(p-toluenesulphonyl)-3-azabicyclo[3.2.0]heptane, 0.26 g of hydrazine monohydrate, and 40 ml of methanol was heated under reflux for 3 hours and cooled to room temperature. The solids thus formed were filtered off. The filtrate was concentrated under reduced pressure. To the residue was added 30 ml of ethyl acetate, and the mixture was stirred at room temperature for 30 min. The solids thus formed were filtered off. The filtrate was concentrated under reduced pressure to give 0.45 g of the titled compound as a pale-yellow oil (yield: 95%).

m.p.: 70°–74° C.

$^1$H-NMR(CDCl$_3$) δ: 7.7–7.6(4H, m), 3.4–2.0(10H, m), 2.3(3H, s), 1.3(3H, s).

Preparation 18: [1α,5α,6α]-6-Amino-1-methyl-3-azabicyclo[3.2.0]heptane

A solution of 0.45 g of [1α,5α,6α]-6-amino-1-methyl-3-(p-toluenesulphonyl)-3-azabicyclo[3.2.0]heptane and 10 ml of an aqueous 48% hydrobromic acid solution was heated under reflux for 3 hours. The resulting solution was concentrated under reduced pressure. The residue was dissolved in 5 ml of water to which 1 ml of an aqueous 40% sodium hydroxide solution was added. The reaction mixture was extracted three times with 20 ml of chloroform. The organic layer was dried over anhydrous sodium sulfate and concentrated under reduced pressure to give 0.19 g of the titled compound as a colorless oil (yield: 95%).

$^1$H-NMR(CDCl$_3$) δ: 3.5–2.5(10H, m), 1.3–1.1(1H, m), 1.26(3H, s).

Preparation 19: [1α,5α,6β]-6-Ethoxycarbonylamino-1-methyl-3-(p-toluenesulphonyl)-3-azabicyclo[3.2.0]heptane To a solution of 4.53 g of [1α,5α,6β]-6-amino-1-methyl-3-(p-toluenesulphonyl)-3-azabicyclo[3.2.0]heptane, 2.46 g of triethylamine and 20 ml of dichloromethane cooled to 0° C. was added dropwise 1.93 g of chloroethyl carbonate. The mixture was stirred at room temperature for an hour. The reaction solution was diluted with 50 ml of dichloromethane, and washed twice with 30 ml of an aqueous 5% hydrochloric acid solution, and once with 30 ml of a saturated aqueous sodium chloride solution. The organic layer was dried over anhydrous magnesium sulfate and concentrated under reduced pressure. The residue was subject to chromatography over silica gel to give 2.8 g of the titled compound as a colorless oil (yield: 49%).

$^1$H-NMR(CDCl$_3$) δ: 7.8–7.3(4H, m), 5.04(1H, d, J=9.45 Hz), 4.5–2.0(8H, m), 4.11(2H, q, J=7.22 Hz), 2.45(3H, s), 1.25(3H, t, J=7.2 Hz), 1.20 (3H, s).

Preparation 20: [1α,5α,6β]-1-Methyl-6-methylamino-3-(p-toluenesulphonyl)-3-azabicyclo[3.2.0]heptane To a solution of 2.80 g of [1α,5α,6β]-6-ethoxycarbonylamino-1-methyl-3-(p-toluenesulphonyl)-3-azabicyclo[3.2.0]heptane and 30 ml of THF was added 0.45 g of lithium aluminum hydride. The mixture was heated under reflux for 10 min. To the reaction solution were added 5 ml of water and 5 ml of an aqueous 20% sodium hydroxide solution in turn. The aqueous layer was separated and concentrated under reduced pressure. The residue was dissolved in 50 ml of ethyl acetate and extracted with 20 ml of an aqueous 10 hydrochloric acid solution. The aqueous solution was adjusted to pH 12 with an aqueous 20% sodium hydroxide solution. The aqueous layer was extracted twice with 30 ml of dichloromethane. The organic layers thus formed were combined together, dried over anhydrous sodium sulfate, and then concentrated under reduced pressure to give 0.85 g of the titled compound as a pale-yellow oil (yield: 36%).

$^1$H-NMR(CDCl$_3$) δ: 7.8–7.3(4H, m), 3.8–1.5(9H, m), 2.44(3H, s), 2.30 (3H, s), 1.20(3H, s)

Preparation 21: [1α,5α,6β]-1-Methyl-6-methylamino-3-azabicyclo[3.2.0]heptane

A solution of 0.82 g of [1α,5α,6β]-1methyl-6-methylamino-3-(p-toluenesulphonyl)-3-azabicyclo[3.2.0]heptane and 10 ml of an aqueous 48% hydrobromic acid solution was heated under reflux for an hour. The reaction mixture was concentrated under reduced pressure. The residue was dissolved in 5 ml of water, adjusted to pH 12 with an aqueous 40 sodium hydroxide solution, and extracted twice with 30 ml of chloroform. The organic layers were combined together, dried over anhydrous sodium sulfate, and then concentrated under reduced pressure to give 0.37 g of the titled compound as a pale-yellow oil (yield: 96%).

$^1$H-NMR(CDCl$_3$) δ: 3.4–1.5(10H, m), 2.28(3H, s), 1.25 (3H, s).

Preparation 22: [1α,6α]-8-Methoxyimino-3-(p-toluenesulphonyl)-3-azabicyclo[4.2.0]octane A mixture of 2.1 g of [1α,6α]-8-oxo-3-(p-toluenesulphonyl)-3-azabicyclo[4.2.0]-octane, 0.82 g of methoxyamine hydrochloride, and 5 ml of pyridine was stirred at room temperature for 2 hours. The mixture was then concentrated under reduced pressure. The residue was dissolved in 20 ml of ethyl acetate. The resulting solution was washed twice with 10 ml of an aqueous 5% hydrochloric acid solution and once with 10 ml of a saturated sodium chloride solution, and then dried over anhydrous magnesium sulfate. The solids thus formed were filtered off under reduced pressure. The filtrate was concentrated under reduced pressure to give 2.3 g of the titled compound as a light-yellow oil (yield: 100%).

$^1$H-NMR(CDCl$_3$) δ: 7.8–7.2(4H, m), 3.8–3.7(3H, s), 3.5–2.5(4H, m), 2.4(3H, s), 2.3–1.1 (6H, m).

Preparation 23: [1α,6α,8β]-8-Amino-3-(p-toluenesulphonyl)-3-azabicyclo[4.2.0]octane To a suspension of 0.8 g of NaBH$_4$ in 20 ml of THF was added a solution of 1.7 ml of TFA in 5 ml of THF at room temperature for 2 hours. Separately, 2.3 g of the titled compound obtained in Preparation 22 was dissolved in 5 ml of THF. The resulting solution was then added to the solution prepared above at room temperature for 2 hours. The reaction mixture was stirred at room temperature for 3 hours, to which 10 ml of water and 5 ml of an aqueous 40% sodium hydroxide solution were added. The mixture was heated under reflux for 5 hours. The resulting solution was concentrated under reduced pressure to remove THF, and extracted three times with 30 ml of dichloromethane. The organic layer was washed with 50 ml of a saturated aqueous sodium chloride solution, and then dried over anhydrous magnesium sulfate. The solids thus formed were filtered off under reduced pressure. The filtrate was concentrated under reduced pressure to give light-yellow solids in foam, which were recrystallized from isopropyl ether to give 1.7 g of the titled compound as white powder (yield: 76%).

m.p.: 112°–116° C.

¹H-NMR(CDCl₃) δ: 7.8–7.2(4H, m), 3.7–2.5(5H, m), 2.4(3H, s), 2.4–1.3 (8H, m).

Preparation 24: [1α,6α,8β]-8-Amino-3-azabicyclo[4.2.0]octane

A mixture of 3.5 g of the titled compound from Preparation 23 and 30 ml of an aqueous 48% hydrobromic acid solution was heated under reflux for 15 hours. The reaction mixture was concentrated under reduced pressure. The residue was dissolved in 5 ml of water, to which 3 ml of an aqueous 40% sodium hydroxide solution was added. The mixture was extracted six times with 100 ml of chloroform. The organic layer was dried over anhydrous sodium sulfate. The solids thus formed were filtered off under reduced pressure. The filtrate was concentrated under reduced pressure to give 1.4 g of the titled compound as a light-yellow oil (yield: 94%).

¹H-NMR(CDCl₃) δ: 3.6–3.2(1H, m), 3.2–2.6(4H, m), 2.6–1.8(5H, m), 1.8–1.2(4H, m).

Preparation 25: (−)-[1α,6α,8β]-8-Amino-3-azabicyclo[4.2.0]octane and (+)-[1α,6α,8β]-8-amino-3-azabicyclo[4.2.0]octane (1) To a suspension of 1.85 g of [1α,6α,8β]-8-amino-3-(p-toluenesulphonyl)-3-azabicyclo[4.2.0]octane and 1.99 g of N-(p-toluenesulphonyl)-L-phenylalanine in 30 ml of dimethylformamide was added 1 ml of triethylamine. After cooling in an ice bath, to the mixture was added 1.2 ml of diethyl cyanophosphonate over 5 minutes. The solution was stirred at the same temperature for 30 minutes, and then continued stirring at room temperature for 3 hours. After adding 200 ml of water, the reaction mixture was extracted twice with ethyl acetate. An organic phase was rinsed once with an aqueous 5% hydrochloric acid solution, washed with water, dried over anhydrous magnesium sulfate, and then concentrated under reduced pressure to give solids in foam. To the solids, 20 ml of ethyl acetate and 10 ml of n-hexane were added. The resulting mixture was heated to dissolve the solids completely. The resulting solution was cooled and then subject to thin layer chromatography (TLC) to give 0.89 g of compound as high polar white solids (Rf=0.3, ethyl acetate:n-hexane=2:1). The filtrate was concentrated under reduced pressure. The concentrate was dissolved completely in 10 ml of ethyl acetate and 5 ml of n-hexane, cooled and subject to a TLC to give 0.96 g of a low polar compound (Rf=0.35, ethyl acetate:n-hexane=2: 1).

(2) To a mixture of 10 ml of an aqueous 48% hydrobromic acid and 5 ml of acetic acid, 0.89 g of the high polar compound from (1) above was added. The resulting solution was heated under reflux overnight, and then concentrated under reduced pressure. The residue was dissolved in 10 ml of water. The solution was adjusted to pH 13–14 with an aqueous 40% sodium hydroxide solution. The resulting mixture was extracted five times with 20 ml of chloroform. The organic layers were combined together, dried over anhydrous sodium sulfate and concentrated under reduced pressure to give 0.17 g of (−)-[1α,6α,8β]-8-amino-3-azabicyclo[4.2.0]octane as a light-yellow oil (yield: 90%).

[α]_D²⁰ −7.1 (C=1.4, MeOH).

¹H-NMR(CDCl₃) δ: 3.6–3.2(1H, m), 3.2–2.6(4H, m), 2.6–1.8(5H, m), 1.8–1.2(4H, m).

(3) In the same manner as in (2) above, 0.96 g of the low polar compound was treated to give 0.19 g of (+)-[1α,6α,8β]-8-amino-3-azabicyclo[4.2.0]octane as a light-yellow oil (yield: 94%).

[α]_D²⁰+6.9(C=1.0, MeOH).

¹H-NMR(CDCl₃) δ: 3.6–3.2(1H, m), 3.2–2.6(4H, m), 2.6–1.8(5H, m), 1.8–1.2(4H,m).

EXAMPLE 1

7-([1α,5α,6β]-6-Amino-1-methyl-3-azabicyclo[3.2.0]heptane-3-yl)1-cyclopropyl-6-fluoro-1,4-dihydro-4-oxoquinoline-3-carboxylicacid, hydrochloride To a suspension of 150 mg of 1-cyclopropyl-6,7-difluoro-1,4-dihydro-4-oxoquinoline-3-carboxylic acid in 5 ml of acetonitrile were added 200 mg of 1,8-diazabicyclo[5,4,0]undec-7-ene (DBU) and 200 mg of [1α,5α,6β]-6-amino-1-methyl-3-azabicyclo[3.2.0]heptane. The reaction mixture was heated under reflux for an hour. The solvent was evaporated out under reduced pressure. To the residue was added 5 ml of an aqueous 5% hydrochloric acid solution. The resulting mixture was stirred at room temperature for 3 hours. The solids were collected by filtration, washed with water and then ethanol, and dried to give 140 mg of the titled compound as pale-yellow solids (yield: 61%).

m.p.: 285°–290° C.

¹H-NMR(DMSO-d₆+TFA-d) δ: 8.55(1H, s), 8.00(1H, d, J=17 Hz), 7.24(1H, d, J=7.4 Hz), 4.3–3.5 (4H, m), 3.5–3.3 (1H, m), 3.0–2.6(2H, m), 2.3–2.0(2H, m), 1.31(3H, s), 1.4–1.0(4H, m).

EXAMPLE 2

7-([1α,5α,6β]-6-Amino-1-methyl-3-azabicyclo[3.2.0.]heptane-3-yl)-1-cyclopropyl-6,8-difluoro-1,4-dihydro-4-oxoquinoline-3-carboxylic acid, hydrochloride To a suspension of 140 mg of 1-cyclopropyl-6,7,8-trifluoro-1,4-dihydro-4-oxo-quinoline-3-carboxylic acid in 3 ml of dimethyl sulfoxide were added 100 mg of K₂CO₃ and 180 mg of [1α,5α,6β]-6-amino-1-methyl-3-azabicyclo[3.2.0]heptane. The reaction mixture was stirred at a temperature of 60°to 80° C. for 4 hours, and then cooled to room temperature. After adding 3 ml of an aqueous 5% hydrochloric acid solution, the mixture was stirred for 2 hours. The solids thus formed were collected by filtration and washed with THF, and then dried to give 70 mg of the titled compound as pale-yellow solids (yield: 33 %).

m.p.: 290°–293° C. (decomp.).

¹H-NMR(DMSO-d₆+TFA-d) δ: 8.69(1H, s), 7.83(1H, dd, J=13.2 Hz, 1.96 Hz), 4.3–3.8(2H, m), 3.8–2.8(4H, m), 2.8–3.0 (3H, m), 1.35(3H, s), 1.3–1.0(4H, m).

EXAMPLE 3

5-Amino-7-([1α,5α,6β]-6-amino-1-methyl-3-azabicyclo[3.2.0]heptane-3-yl)-3-cyclopropyl-6,8-difluoro-1,4-dihydro-4-oxoquinoline-3-carboxylic acid To a suspension of 70 mg of 5-amino-1-cyclopropyl-6,7,8-trifluoro-1,4-dihydro-4-oxoquinoline-3-carboxylic acid in 3 ml of acetonitrile were added 120 mg of DBU and 150 mg of [1α,6α,8β]-6-amino-1-methyl-3-azabicyclo[3.2.0]heptane. The resulting mixture was heated under reflux for 3 hours. The reaction mixture was cooled to room temperature, neutralized with an aqueous 10% hydrochloric acid solution, and then stirred at room temperature for an hour. The solids thus formed were collected by filtration, washed with water, and then dried to give 60 mg of the titled compound as yellow solids (yield: 63%).

m.p.: 195°–200° C. (decomp.).

¹H-NMR(DMSO-d₆+TFA-d) δ: 8.3(1H, s), 4.1–3.1(5H, m), 3.0–2.5(2H, m), 2.4–2.0(2H, m), 1.25(3H, s), 1.2–0.9 (4H, m).

EXAMPLE 4

7-([1α,6α,8β]-6-Amino-1-methyl-3-azabicyclo[3.2.0]heptane-3-yl)-6,8-difluoro-1-(2,4-difluorophenyl)-1,4-dihydro-4-oxoquinoline-3-carboxylic acid To a suspension of 100 mg of 1-(2,4-difluorophenyl)-6,7,8-trifluoro-1,4-dihydro-4-oxoquinoline-3-carboxylic acid in 3 ml of acetonitrile were added 110 mg of DBU and 150 mg of [1α,6α,8β]-6-amino-1-methyl-3-azabicyclo[3.2.0]heptane. The reaction mixture was heated under reflux for 2 hours and concentrated under reduced pressure. The residue was dissolved in 2 ml of water, neutralized with an aqueous 10% hydrochloric acid solution, and stirred at room temperature for an hour. The solids were collected by filtration, washed with water, and then dried to give 100 mg of the titled compound as pale yellow solids (yield: 89 %).

m.p.: 135°–140° C.

$^1$H-NMR(DMSO-d$_6$+TFA-d) δ: 8.5(1H, s), 8.0–7.0(5H, m), 4.0–3.0(5H, m), 2.9–2.5(2H, m), 2.4–1.9(2H, m), 1.2 (3H, s).

EXAMPLE 5

7-([1α,5α,6β]-6-Amino-1-methyl-3-azabicyclo[3.2.0]-heptane-3-yl)-1-cyclopropyl-6,8-difluoro-5-methyl-1,4-dihydro-4-oxoquinoline-3-carboxylic acid To a suspension of 100 mg of 1-cyclopropyl-5-methyl-6,7,8-trifluoro-1,4-dihydro-4-oxoquinoline-3-carboxylic acid in 2 ml of acetonitrile were added 100 mg of DBU and 150 mg of [1α,5α,6β]-6-amino-1-methyl-3-azabicyclo[3.2.0] heptane. The reaction mixture heated under reflux for an hour and concentrated under reduced pressure. The residue was dissolved in 2 ml of water, neutralized with an aqueous 10% hydrochloric acid solution, and stirred at room temperature for an hour. The solids were collected by filtration, washed with water, and then dried to give 70 mg of the titled compound as yellow solids (yield: 47%).

m.p.: 275°–280° C.

$^1$H-NMR(DMSO-d$_6$+TFA-d) δ: 8.5(1H, s), 4.1–3.5(5H, m), 3.0–2.5(2H, m), 2.6(3H, d, J=3.0 Hz), 2.3–2.0(2H, m), 1.2(3H, s), 1.2–0.8(4H, m).

EXAMPLE 6

7-([1α,5α,6β]-6-Amino-1-methyl-3-azabicyclo[3.2.0] heptane-3-yl)-8-chloro-1-cyclopropyl-6-fluoro-1,4-dihydro-4-oxoquinoline-3-carboxylic acid To a suspension of 100 mg of 8-chloro-1-cyclopropyl-6,7-difluoro-1,4-dihydro-4-oxoquinoline-3-carboxylic acid in 2 ml of acetonitrile were added 100 mg of DBU and 70 mg of [1α,5α,6β]-6-amino-1-methyl-3-azabicyclo[3.2.0] heptane. The reaction mixture was heated under reflux for 5 hours and concentrated under reduced pressure. The residue was dissolved in 2 ml of water, neutralized with an aqueous 10% hydrochloric acid solution, and stirred at room temperature for an hour. The resulting solids were collected by filtration, washed with water, and then dried to give 40 mg of the titled compound as pale-yellow solids (yield: 30%).

m.p.: 222°–225° C.

$^1$H-NMR(DMSO-d$_6$+TFA-d) δ: 8.77(1H, s), 7.86(1H, d, J=12.8 Hz), 4.5–4.0 (1H, m), 4.0–3.2(4H, m), 2.9–2.5(2H, m), 2.3–2.0(2H, m), 1.25(3H, s), 1.1–0.7(4H, m).

EXAMPLE 7

7-([1α,5α,6β]-6-Amino-1-methyl-3-azabicyclo[3.2.0] heptane-3-yl)-1-cyclopropyl-6-fluoro-1,4-dihydro-4-oxo-1,8-naphthyridine-3-carboxylic acid To a suspension of 100 mg of 7-chloro-1-cyclopropyl-6-fluoro-1,4-dihydro-4-oxo-1,8-naphthyridine-3-carboxylic acid in 2 ml of acetonitrile were added 120 mg of DBU and 150 mg of [1α,5α,6β]-6-amino-1-methyl-3-azabicyclo [3.2.0]heptane. The reaction mixture was heated under reflux for 2 hours and concentrated under reduced pressure. The residue was dissolved in 2 ml of water, neutralized with an aqueous 10% hydrochloric acid solution, and stirred at room temperature for an hour. The solids were collected by filtration, washed with water, and then dried to give 100 mg of the titled compound as pale-yellow solids (yield: 77 m.p.: >270° C.

$^1$H-NMR(CDCl$_3$) δ: 8.67(1H, s), 8.00(1H, d, J=12.7 Hz), 4.7–4.3(1H, m), 4.2–3.1(6H, m), 2.7–2.1(2H, m), 1.27(3H, s), 1.1–0.8(4H,m).

EXAMPLE 8

7-([1α,5α,6β]-6-Amino-1-methyl-3-azabicyclo[3.2.0] heptane-3-yl)-1-(2,4-difluorophenyl)-6-fluoro-1,4-dihydro-4-oxo-1,8-naphthyridine-3-carboxylic acid To a suspension of 100 mg of 7-chloro-1-(2,4-difluorophenyl)-6-fluoro-1,4-dihydro-4-oxo-1,8-naphthyridine-3-carboxylic acid in 2 ml of acetonitrile were added 100 mg of DBU and 150 mg of [1α,5α,6β]-6-amino-1-methyl-3-azabicyclo[3.2.0]heptane. The reaction mixture was heated under reflux for 2 hours and concentrated under reduced pressure. The residue was dissolved in 2 ml of water, neutralized with an aqueous 10% hydrochloric acid solution, and stirred at room temperature for an hour. The solids were collected by filtration, washed with water, and then dried to give 110 mg of the titled compound as pale-yellow solids (yield: 88%).

m.p.: 120°–125° C.

$^1$H-NMR(DMSO-d$_6$+TFA-d) δ: 8.7(1H, s), 8.0(1H, d, J=12.7 Hz), 7.8–7.0 (3H, m), 4.0–3.2(4H, m), 3.1–2.5(2H, m), 2.2–1.8(2H, m), 1.2(3H, s).

EXAMPLE 9

7-([1α,5α,6β]-6-Amino-1-methyl-3-azabicyclo[3.2.0] heptane-3-yl)-6-fluoro-1-(4-fluorophenyl)-1,4-dihydro-4-oxo-1,8-naphthyridine-3-carboxylic acid To a suspension of 60 mg of 7-chloro-6-fluoro-1-(4-fluorophenyl)-1,4-dihydro-4-oxo-1,8-naphthyridine-3-carboxylic acid in 2 ml of acetonitrile were added 100 mg of DBU and 100 mg of [1α,5α,6β]-6-amino-1-methyl-3-azabicyclo[3.2.0]heptane was stirred at room temperature for 2 hours and concentrated under reduced pressure. The residue was dissolved in 2 ml of water, neutralized with an aqueous 10% hydrochloric acid solution, and stirred at room temperature for an hour. The solids were collected by filtration, washed with water, and then dried to give 50 mg of the titled compound as pale-yellow solids (yield: 67%).

m.p.: 248°–252° C. (decomp.).

$^1$H-NMR(DMSO-d$_6$+TFA-d) δ: 8.62(1H, s), 8.00(1H, d, J=16.0 Hz), 7.1(4H, m), 4.1–3.2(4H, m), 3.1–2.5(2H, m), 2.3–1.8 (2H, m), 1.23 (3H, s).

EXAMPLE 10

7-([1α,5α,6β]-6-Amino-1-methyl-3-azabicyclo[3.2.0] heptane-3-yl)-1-t-butyl-6-fluoro-1,4-dihydro-4-oxo-1,8-naphthyridine-3-carboxylic acid To a suspension of 100 mg of 1-t-butyl-7-chloro-6-fluoro-1,4-dihydro-4-oxo-1,8-naphthyridine-3-carboxylic acid in 2 ml of acetonitrile were added 80 mg of DBU and 70 mg of [1α,5α,6β]-6-amino-1-methyl-3-azabicyclo[3.2.0]heptane. The reaction mixture was stirred at room temperature for 5 hours and concentrated under reduced pressure. The residue was dissolved in 2 ml of water, neutralized with an aqueous 10% hydrochloric acid solution, and stirred at room temperature for an hour. The solids were collected by filtration, washed with water, and then dried to give 60 mg of the titled compound as white solids (yield: 48%).

m.p.: 130°–135° C.

$^1$H-NMR(DMSO-d$_6$+TFA-d) δ: 8.86(1H, s), 8.05(1H, d, J=13.0 Hz), 4.5–2.0 (8H, m), 1.90(9H, s), 1.38(3H, s).

EXAMPLE 11

7-([1α,5α,6β]-6-Amino-1-methyl-3-azabicyclo[3.2.0] heptane-3-yl)-1-(2,4-difluorophenyl)-6-fluoro-5-methyl-1,4-dihydro-4-oxo-1,8-naphthyridine-3-carboxylic acid To a suspension of 80 mg of 7-chloro-1-(2,4-difluorophenyl)-6-fluoro-5-methyl-1,4-dihydro-4-oxo-1,8-naphthyridine-3-carboxylic acid in 2 ml of acetonitrile were added 70 mg of DBU and 70 mg of [1α,5α,6β]-6-amino-1-methyl-3-azabicyclo[3.2.0]heptane. The reaction mixture was stirred at room temperature for 4 hours and concentrated under reduced pressure. The residue was dissolved in 2 ml of water, neutralized with an aqueous 10% hydrochloric acid solution, and stirred at room temperature for an hour. The solids were collected by filtration, washed with water, and then dried to give 90 mg of the titled compound as pale-yellow solids (yield: 91%).

m.p.: 110°–115° C.

$^1$H-NMR(DMSO-$d_6$+TFA-d) δ: 8.6(1H, s), 7.5–6.9(3H, m), 4.5–2.0(10H, m), 2.8(3H, d, J=3.3 Hz), 1.3(3H, s).

EXAMPLE 12

(+)-7-([1α,5α,6β]-6-Amino-1-methyl-3-azabicyclo[3.2.0]heptane-3-yl)-1-cyclopropyl-6-fluoro-1,4-dihydro-4-oxo-1,8-naphthyridine-3-carboxylic acid To a suspension of 400 mg of 7-chloro-1-cyclopropyl-6-fluoro-1,4-dihydro-4-oxo-1,8-naphthyridine-3-carboxylic acid in 10 ml of acetonitrile were added 320 mg of DBU and 300 mg of (−)-[1α,5α,6β]-6-amino-1-methyl-3-azabicyclo[3.2.0]heptane. The reaction mixture was stirred at room temperature for 3 hours. The solids were collected by filtration, washed with a small amount of acetonitrile, and then dried to give 400 mg of the titled compound as white solids (yield: 76%).

To a suspension of 400 mg of the titled compound thus obtained in 8 ml of methanol was added 1.2 ml of an aqueous 1N hydrochloric acid solution dropwise at room temperature, and the mixture was stirred continuously for an hour. The solids thus formed were collected by filtration under reduced pressure, washed with 5 ml of ethanol, and then dried to give 4.2 g of the titled compound, in the form of hydrochloride, as white solids (yield: 95%).

m.p.: >270° C.

$[α]_D^{20}$+17.2° (C=0.5, 1N-NaOH).

$^1$H-NMR(CDCl$_3$) δ: 8.67(1H, s), 8.00(1H, d, J=12.7 Hz), 4.7–4.3(1H, m), 4.2–3.1(6H, m), 2.7–2.1(2H, m), 1.27(3H, s), 1.1–0.8 (4H, m).

EXAMPLE 13

(−)-7-([1α,5α,6β]-6-Amino-1-methyl-3-azabicyclo[3.2.0]heptane-3-yl)-1-cyclopropyl-6,8-difluoro-1,4-dihydro-4-oxoquinoline-3-carboxylic acid, hydrochloride To a suspension of 50 mg of 1-cyclopropyl-6,7,8-trifluoro-1,4-dihydro-4-oxoquinoline-3-carboxylic acid in 2 ml of acetonitrile were added 70 mg of DBU and 60 mg of (−)-[1α,5α,6β]-6-amino-1-methyl-3-azabicyclo[3.2.0]heptane. The reaction mixture was heated under reflux for 5 hours and concentrated under reduced pressure. The residue was dissolved in 2 ml of water, and adjusted to pH 1 with an appropriate amount of an aqueous concentrated hydrochloric acid solution. The solids thus formed were collected by filtration, washed with isopropyl alcohol, and then dried to give 30 mg of the titled compound as pale-yellow solids (yield: 34%).

m.p.: >270° C.

$^1$H-NMR(DMSO-$d_6$+TFA-d) δ: 8.69 (1H, s), 7.83 (1H, dd, J=13.2 Hz, 1.96 Hz), 4.3–3.8(2H, m), 3.8–2.8(4H, m), 2.8–2.0 (3H, m), 1.35(3H, s), 1.3–1.0(4H, m).

EXAMPLE 14

(+)-7-([1α,5α,6β]-6-Amino-1-methyl-3-azabicyclo[3.2.0]heptane-3-yl)-1-cyclopropyl-6,8-difluoro-1,4-dihydro-4-oxoquinoline-3-carboxylic acid, hydrochloride To a suspension of 100 mg of 1-cyclopropyl-6,7,8-trifluoro-1,4-dihydro-4-oxo-quinoline-3-carboxylic acid in 2 ml of acetonitrile were added 130 mg of DBU and 110 mg of (+)-[1α,5α,6β]-6-amino-1-methyl-3-azabicyclo[3.2.0]heptane. The reaction mixture was heated under reflux for 3 hours and concentrated under reduced pressure. The residue was dissolved in 2 ml of water, and adjusted to pH 1 with an appropriate amount of an aqueous concentrated hydrochloric acid solution. The solids thus formed were collected by filtration, washed with isopropyl alcohol, and then dried to give 60 mg of the titled compound as pale-yellow solids (yield: 41%).

m.p.: >270° C.

$^1$H-NMR(DMSO-$d_6$+TFA-d) δ: 8.69(1H, s), 7.83(1H, dd, J=13.2 Hz, 1.96 Hz), 4.3–3.8(2H, m), 2.8–2.0(4H, m), 1.35(3H, s), 1.3–1.0(4H, m).

EXAMPLE 15

1-Cyclopropyl-6,8-difluoro-7-([1α,5α,6β]-6-hydroxy-1-methyl-3-azabicyclo[3.2.0]heptane-3-yl)-1,4-dihydro-4-oxoquinoline-3-carboxylic acid To a suspension of 150 mg of 1-cyclopropyl-6,7,8-trifluoro-1,4-dihydro-4-oxoquinoline-3-carboxylic acid in 3 ml of acetonitrile were added 160 mg of DBU and 150 mg of [1α,5α,6β]-6-hydroxy-1-methyl-3-azabicyclo[3.2.0]heptane. The reaction mixture was heated under reflux for 4 hours and stirred at room temperature overnight. The solids thus formed were collected by filtration, washed with a small amount of acetonitrile, and then dried to give 170 mg of the titled compound as white solids (yield: 82%).

m.p.: 215°–218° C. (decomp.).

$^1$H-NMR(DMSO-$d_6$+TFA-d) δ: 8.65 (1H, s), 7.76 (1H, dd, J=13.6 Hz, 1.9 Hz), 4.5–3.9(2H, m), 3.7–3.1(4H, m), 2.7–1.8 (3H, m), 1.3(3H, s), 1.2–1.0(4H, m).

EXAMPLE 16

1-Cyclopropyl-6-fluoro-7-([1α,5α,6β]-6-hydroxy-1-methyl-3-azabicyclo[3.2.0]-heptane-3-yl)-1,4-dihydro-4-oxo-1,8-naphthyridine-3-carboxylic acid To a suspension of 100 mg of 7-chloro-1-cyclopropyl-6-fluoro-1,4-dihydro-4-oxo-1,8-naphthyridine-3-carboxylic acid in 3 ml of acetonitrile were added 150 mg of DBU and 130 rag of [1α,5α,6β]-6-hydroxy-1-methyl-3-azabicyclo[3.2.0]heptane. The reaction mixture was heated under reflux for an hour, concentrated under reduced pressure, and stirred at room temperature for an hour. The solids thus formed were collected by filtration, washed with a small amount of acetonitrile, and then dried to give 70 mg of the titled compound as pale-yellow solids (yield: 53%).

m.p.: 265° C. (decomp.).

$^1$H-NMR(DMSO-$d_6$+TFA-d) δ: 8.55(1H, s), 7.93(1H, d, J=13.0 Hz), 4.7–3.1 (6H, m), 2.8–2.0(3H, m), 1.32(3H, s), 1.3–0.9(4H, m).

EXAMPLE 17

(−)-7-([1α,5α,6β]-6-amino-1-methyl-3-azabicyclo[3.2.0]heptane-3-yl)-1-cyclopropyl-6,8-difluoro-5-methyl-1,4-dihydro-4-oxoquinoline-3-carboxylic acid To a suspension of 300 mg of 1-cyclopropyl-5-methyl-6,7,8-trifluoro-1,4-dihydro-4-oxoquinoline-3-carboxylic acid in 10 ml of acetonitrile were added 230 mg of DBU and 190 mg of (−)-[1α,5α,6β]-6-amino-1-methyl-3-azabicyclo[3.2.0]heptane. The reaction mixture was stirred at 60° C. for 8 hours and concentrated under reduced pressure. The residue was dissolved in 3 ml of water, neutralized with an aqueous 10% hydrochloric acid solution, and stirred at room temperature for 2 hours. The solids were collected by filtration, washed with water, and then dried to give 340 mg of the titled compound as white solids (yield: 84%).

m.p.: 275°–280° C.

$[\alpha]_D^{20}$ –221.2° (C=0.5, DMSO).

$^1$H-NMR(DMSO$_6$) δ: 8.64(1H, s), 4.3–2.0(9H, m), 2.71 (3H, d, J=3.15 Hz), 1.33(3H, s), 1.2–0.9(4H, m).

EXAMPLE 18

(–)-5-Amino-7-([1α,5α,6β]-6-amino-1-methyl-3-azabicyclo[3.2.0]heptane-3-yl)-1-cyclopropyl-6,8-difluoro-1,4-dihydro-4-oxoquinoline-3-carboxylic acid To a suspension of 300 mg of 5-amino-1-cyclopropyl-6,7,8-trifluoro-1,4-dihydro-4-oxoquinoline-3-carboxylic acid in 3 ml of dimethylsulfoxide(DMSO) was added 190 mg of (–)-[1α,5α,6β]-6-amino-1-ethyl-3-azabicyclo[3.2.0]heptane. The reaction mixture was stirred at 60° C. for 5 hours, and then cooled to room temperature. After adding 10 ml of water, the resulting mixture was stirred for 2 hours. The solids thus formed were collected by filtration, washed with water, and then dried to give 340 mg of the titled compound as yellow solids (yield: 83%).

m.p.: 196°–200° C. (decomp.).

$[\alpha]_D^{20}$ –280.6° (C=0.5, DMSO).

$^1$H-NMR(DMSO-d$_6$) δ:8.49(1H, s), 7.19(2H, s), 4.3–2.0 (9H, m), 1.34(3H, s), 1.3–0.8(4H, m).

EXAMPLE 19

(–)-7-([1α,5α,6β]-6-Amino-1-methyl-3-azabicyclo[3.2.0]heptane-3-yl)-1-t-butyl-6-Fluoro-1,4-dihydro-4-oxo-1,8-naphthyridine-3-carboxylic acid To a suspension of 300 mg of 1-tert.-butyl-7-chloro-6-fluoro-1,4-dihydro-4-oxo-1,8-naphthyridine-3-carboxylic acid in 5 ml of acetonitrile were added 200 mg of DBU and 150 mg of (–)-[1α,5α,6β]-6-amino-1-methyl-3-azabicyclo[3.2.0]heptane. After stirring at 70° C. for 2 hours, the reaction mixture was cooled to room temperature and concentrated under reduced pressure. The residue was dissolved in 3 ml of water, neutralized with an aqueous 5% hydrochloric acid solution, and stirred at room temperature for 2 hours. The solids were collected by filtration, washed with water, and then dried to give 260 mg of the titled compound as pale-yellow solids (yield: 67%).

m.p.: 134°–138° C.

$[\alpha]_D^{20}$ –20.4° (C=0.5, DMSO).

$^1$H-NMR(DMSO-d$_6$) δ: 8.87(1H, s), 8.06(1H, d, J=12.9 Hz), 4.5–2.0(8H, m), 1.90(9H, s), 1.39(3H, s).

EXAMPLE 20

(–)-7-([1α,5α,6β]-6-Amino-1-methyl-3-azabicyclo[3.2.0]heptane-3-yl)-8-chloro-1-cyclopropyl-6-fluoro-1,4-dihydro-4-oxoquinoline-3-carboxylic acid To a suspension of 300 mg of 8-chloro-1-cyclopropyl-6,7-difluoro-1,4-dihydro-4-oxo-quinoline-3-carboxylic acid in 4 ml of acetonitrile were added 190 mg of DBU and 150 mg of (–)-[1α,5α,6β]-6-amino-1-methyl-3-azabicyclo[3.2.0]heptane. After stirring at 50° C. for 3 hours, the reaction mixture was continued to stir at room temperature overnight. The solids thus formed were collected by filtration, washed with a small amount of acetonitrile, and then dried to give 290 mg of the titled compound as white solids (yield: 71%).

m.p.: 222°–228° C.

$[\alpha]_D^{20}$ –111.2° (C=0.5, DMSO).

$^1$H-NMR(DMSO-d$_6$) δ: 8.77(1H, s), 7.88(1H, d, l=12.8 Hz), 4.5–4.0(1H, m), 4.0–3.2(4H, m), 2.9–2.5(2H, m), 2.3–2.0 (2H, m), 1.25(3H, s), 1.0–0.7(4H, m).

EXAMPLE 21

(–)-7-([1α,5α,6β]-6-Amino-1-methyl-3-azabicyclo[3.2.0]heptane-3-yl)-1-(2,4-difluorophenyl)-6-fluoro-1,4-dihydro-4-oxo-1,8-naphthyridine-3-carboxylic acid To a suspension of 200 mg of 7-chloro-1-(2,4-difluorophenyl)-6-fluoro-1,4-dihydro-4-oxo-1,8-naphthyridine-3-carboxylic acid in 2 ml of acetonitrile were added 140 mg of DBU and 140 mg of (–)-[1α,5α,6β]-6-amino-1-methyl-3-azabicyclo[3.2.0]heptane. The reaction mixture was stirred at room temperature for 12 hours and concentrated under reduced pressure. The residue was dissolved in 3 ml of water, neutralized with an aqueous 5% hydrochloric acid solution, and stirred at room temperature for 2 hours. The solids thus formed were collected by filtration, washed with water, and then dried to give 210 mg of the titled compound as white solids (yield: 84%).

m.p.: 123°–127° C.

$[\alpha]_D^{20}$ –17.0° (C=0.5, DMSO).

$^1$H-NMR(DMSO-d$_6$+TFA-d) δ: 8.7(1H, s), 8.0(1H, d, J=12.7 Hz), 7.8–7.0 (3H, m), 4.0–3.2(4H, m), 3.1–2.5(2H, m), 2.2–1.8(2H, m), 1.2(3H, s).

EXAMPLE 22

(–)-7-([1α,5α,6β]-6-Amino-1-methyl-3-azabicyclo[3.2.0]heptane-3-yl)-6-fluoro-1-(4-fluorophenyl)-1,4-dihydro-4-oxo-1,8-naphthyridine-3-carboxylic acid To a suspension of 200 mg of 7-chloro-6-fluoro-1-(4-fluorophenyl)-1,4-dihydro-4-oxo-1,8-naphthyridine-3-carboxylic acid in 2 ml of acetonitrile were added 140 mg of DBU and 140 mg of (–)-[1α,5α,6β]-6-amino-1-methyl-3-azabicyclo[3.2.0]heptane. The reaction mixture was stirred at room temperature for 12 hours and concentrated under reduced pressure. The residue was dissolved in 3 ml of water, neutralized with an aqueous 5% hydrochloric acid solution, and stirred at room temperature for 2 hours. The solids were collected by filtration, and washed with water, then dried to give 140 mg of the titled compound as white solids (yield: 56%).

m.p.: 250°–253° C.

$[\alpha]_D^{20}$ –37.6° (C=0.5, DMSO).

$^1$H-NMR(DMSO-d$_6$+TFA-d) δ: 8.6(1H, s), 8.0(1H, d, J=16.0 Hz), 7.8–7.1 (4H, m), 4.1–3.2(4H, m), 3.1–2.5(2H, m), 2.3–1.8(2H, m), 1.2(3H, s).

EXAMPLE 23

7-([1α,5α,6β]-6-Amino-5-methyl-3-azabicyclo[3.2.0]heptane-3-yl)-6,8-difluoro-1-cyclopropyl-1,4-dihydro-1,4-oxoquinoline-3-carboxylic acid To a suspension of 120 mg of 1-cyclopropyl-1,4-dihydro-6,7,8-trifluoro-4-oxo-3-quinoline carboxylic acid in 10 ml of acetonitrile were added 100 mg of DBU and 150 mg of [1α,5α,6β]-6-amino-5-methyl-3-azabicyclo[3.2.0]heptane. After refluxing at 80°C. for 10 hours, the reaction mixture was cooled to room temperature and allowed to stand overnight. The solids thus formed were collected by filtration under reduced pressure, washed with isopropyl ether, and then dried to give 90 mg of the titled compound (yield: 55%).

m.p.: 235°–240° C. (decomp.).

$^1$H-NMR(DMSO-d$_6$+TFA-d) δ: 8.68(1H, s), 8.08(2H, brs), 7.81(1H, dd, J=2 Hz, 12 Hz), 4.2–3.5(6H, m), 3.0–2.5 (1H, m), 2.0–1.6(2H, m), 1.4 (3H, s), 1.2–0.9(4H, m).

EXAMPLE 24

7-([1α,5α,6β]-6-Amino-5-methyl-3-azabicyclo[3.2.0]heptane-3-yl)-8-fluoro-1-(4-fluorophenyl)-1,4-dihydro-4-oxo-1,8-naphthyridine-3-carboxylic acid To a suspension of 200 mg of 7-chloro-1,4-dihydro-1-(4-fluorophenyl)-6-fluoro-4-oxo-1,8-naphthyridine-3-carboxylic acid in 5 ml of acetonitrile were added 110 mg of DBU and 100 mg of [1α,5α,6β]-6-amino-5-methyl-3- azabicyclo[3.2.0]heptane. The mixture was stirred at room temperature for an hour. The solvent was evaporated out under reduced pressure. The residue was dissolved in 2 ml of distilled water. The resulting solution was neutralized with an aqueous 10% hydrochloric acid solution and stirred at room temperature for 2 hours. The solids thus formed were collected by filtration, washed with a small amount of distilled water and then with isopropyl ether, and then dried to give 220 mg of the titled compound (yield: 79%).

m.p.: 253°–255° C. (decomp.).

$^1$H-NMR(DMSO-$d_6$+TFA-d) δ: 8.63(1H, s), 8.05(1H, d, J=12.9 Hz), 7.6–7.3 (4H, m), 4.4–4.1(1H, m), 3.70–3.05(4H, m), 2.5–2.1(2H, m), 1.7–1.3(1H, m), 1.22(3H, s).

EXAMPLE 25

8-Chloro-1-cyclopropyl-7-([1α,5α,6β]-6-amino-5-methyl-3-azabicyclo[3.2.0]heptane-3-yl)-6-fluoro-1,4-dihydro-4-oxo-3-quinoline carboxylic acid To a suspension of 200 mg of 8-chloro-1-cyclopropyl-6,7-difluoro-1,4-dihydro-4-oxo-3-quinoline carboxylic acid in 5 ml of acetonitrile were added 130 mg of DBU and 100 mg of [1α,5α,6β]-6-amino-5-methyl-3-azabicyclo[3.2.0]heptane. The mixture was refluxed at 80° C. for 4 hours. The solvent was evaporated out under reduced pressure. The residue was dissolved in 3 ml of distilled water. The resulting solution was neutralized with an aqueous 5% hydrochloric acid solution and stirred at room temperature for 2 hours. The solids thus formed were collected by filtration under reduced pressure, washed with distilled water and then with isopropyl ether, and then dried to give 140 mg of the titled compound (yield: 54%).

m.p.: 175°–178° C.

$^1$H-NMR(DMSO-$d_6$+TFA-d) δ: 8.85(1H, s), 7.91(1H, d, J=12.8 Hz), 4.5–4.3 (1H, m), 3.9–3.7(1H, m), 3.6–3.0(4H, m), 2.5–2.3 (2H, m), 2.0–1.8(1H, m), 1.34(3H, s), 1.1–0.9 (4H, m).

EXAMPLE 26

7-([1α,5α,6β]-6-Amino-5-methyl-3-azabicyclo[3.2.0]heptane-3-yl)-1-cyclopropyl-6-fluoro-1,4-dihydro-4-oxo-1,8-naphthyridine-3-carboxylic acid To a suspension of 180 mg of 7-chloro-1-cyclopropyl-1,4-dihydro-6-fluoro-4-oxo-1,8-naphthyridine-3-carboxylic acid in 5 ml of acetonitrile were added 130 mg of DBU and 100 mg of [1α,5α,6β]-6-amino-5-methyl-3-azabicyclo [3.2.0]heptane. The reaction mixture was stirred at 50° C. for 1.5 hours and cooled to room temperature. The solids thus formed were collected by filtration, washed with isopropyl alcohol, and then dried to give 200 mg of the titled compound (yield: 84%).

m.p.: 265°–270° C. (decomp.).

$^1$H-NMR(DMSO-$d_6$+TFA-d) δ: 8.55(1H, s), 7.94(1H, d, J=12.9 Hz), 4.5–4.3 (1H, m), 4.1–3.8(1H, m), 3.7–3.3(4H, m), 2.7–2.4(2H, m), 1.9–1.6(1H, m), 1.37(3H, s), 1.3–1.1 (4H, m).

EXAMPLE 27

1-(2,4-Difluorophenyl)-7-([1α,5α,6β]-6-amino-5-methyl-3-azabicyclo[3.2.0]heptane-3-yl)-6-fluoro-1,4-dihydro-4-oxo-1,8-naphthyridine-3-carboxylic acid To a suspension of 200 mg of 7-chloro-1-(2,4-difluorophenyl)-1,4-dihydro-6-fluoro-4-oxo-1,8-naphthyridine-3-carboxylic acid in 5 ml of acetonitrile were added 110 mg of DBU and 100 mg of [1α,5α,6β]-6-amino-5-methyl-3-azabicyclo[3.2.0]heptane. The mixture was stirred at 30° to 40° C. for an hour. The solvent was evaporated out under reduced pressure. The residue was dissolved in 2 ml of distilled water. The resulting solution was adjusted to pH 6–7 with an aqueous 5% hydrochloric acid solution and stirred in an ice bath for 30 minutes. The solids thus formed were collected by filtration, washed with a small amount of distilled water and then with isopropyl ether, and then dried to give 220 mg of the titled compound (yield: 88%).

m.p.: 110°–115° C.

$^1$H-NMR(DMSO-$d^6$+TFA-d) δ: 8.80(1H, s), 8.08(1H, d, J=12.7 Hz), 7.9–7.2 (3H, m), 4.2–4.0(1H, m), 3.6–3.1(4H, m), 2.7–2.3(2H, m), 1.8–1.5(1H, m), 1.27(3H, s).

EXAMPLE 28

(–)-7-([1α,5α,6β]-6-Amino-1-methyl-3-azabicyclo[3.2.0]heptane-3-yl)-1-(2,4-difluorophenyl)-1,4-dihydro-6-fluoro-5-methyl-4-oxo-1,8-naphthyridine-3-carboxylic acid To a suspension of 100 mg of 7-chloro-1-(2,4-difluorophenyl)-1,4-dihydro-6-fluoro-5-phenyl-4-oxo-1,8-naphthyridine-3-carboxylic acid in 4 ml of acetonitrile were added 80 mg of DBU and 70 mg of (–)-[1α,5α,6β]-6-amino-1-methyl-3-azabicyclo [3.2.0]heptane. The reaction mixture was stirred at 50° C. for 3 hours. The solvent was evaporated out under reduced pressure. The residue was dissolved in 1 ml of distilled water. The resulting solution was neutralized with an aqueous 5% hydrochloric acid solution. The resulting solids were collected by filtration, washed with isopropyl ether, and then dried to give 100 mg of the titled compound (yield: 80.6%).

m.p.: 113°–115° C.

$^1$H-NMR(CDCl$_3$) δ: 8.6(1H, s), 7.6–6.8(3H, m), 4.5–2.0 (10H, m), 2.8 (3H, d, J=3.2 Hz), 1.3(3H, s).

EXAMPLE 29

1-Cyclopropyl-7-([1α,5α,6β]-6-hydroxy-3-azabicyclo[3.2.0]heptane-3-yl)-6,8-difluoro-1,4-dihydro-4-oxo-3-quinoline carboxylic acid To a suspension of 250 mg of 1-cyclopropyl-6,7,8-trifluoro-1,4-dihydro-4-oxo-3-quinoline carboxylic acid in 5 ml of dimethyl sulfoxide was added 250 mg of [1α,5α,6β]-6-hydroxy-3-azabicyclo[3.2.0.]heptane. The reaction mixture was refluxed at 60° to 80° C. for 8 hours and then cooled to room temperature. Into the mixture, 5 ml of distilled water was poured. The solids thus formed were collected by filtration, washed with isopropyl alcohol, and then dried to give 280 mg of the titled compound (yield: 84.3%).

m.p.: 235°–240° C.

$^1$H-NMR(DMSO-$d_6$+TFA-d) δ: 8.26(1H, s), 7.71(1H, dd, J=2.0 Hz, J=12 Hz), 4.8–4.4 (3H, m), 3.9–3.3(4H, m), 3.2–2.85 (1H, m), 2.8–2.2(2H, m), 1.9–1.5(1H, m), 1.4–1.05 (4H, d, J=6.2 Hz)

EXAMPLE 30

5-Amino-1-cyclopropyl-7-([1α,5α,6β]-6-hydroxy-3-azabicyclo[3.2.0]heptane-3-yl)-6,8-difluoro-1,4-dihydro-4-oxo-3-quinoline-carboxylic acid To a suspension of 300 mg of 5-amino-1-cyclopropyl-6,7,8-trifluoro-1,4-dihydro-4-oxo-3-quinoline carboxylic acid in 5 ml of dimethyl sulfoxide was added 250 mg of [1α,5α,6β]-6-hydroxy-3-azabicyclo[3.2.0]heptane. The reaction mixture was refluxed at 90° C. for 5 hours and then cooled to room temperature. Into the mixture, 5 ml of distilled water was poured. The solids thus formed were collected by filtration, washed with isopropyl alcohol, and then dried to give 150 mg of the titled compound (yield: 38%).

m.p.: 220° C. (decomp.).

$^1$H-NMR(DMSO-$d_6$+TFA-d) δ: 8.48(1H, s), 4.4–3.8(3H, m), 3.8–2.8(5H, m), 2.6–2.2(2H, m), 1.9–1.5(1H, m), 1.3–0.9 (4H, m).

EXAMPLE 31

1-Cyclopropyl-7-([1α,5α,6β]-6-hydroxy-3-azabicyclo[3.2.0]heptane-3-yl)-6,8-difluoro-1,4-dihydro-5-methyl-4-oxo-3-quinoline-carboxylic acid To a suspension of 110 mg of 1-cyclopropyl-1,4-dihydro-5-methyl-6,7,8-trifluoro-4-oxo-3-quinoline carboxylic acid in 3 ml of acetonitrile were added 100 mg of DBU and 100 mg of [1α,5α,6β]-6-hydroxy-3-azabicyclo[3.2.0]heptane. The reaction mixture was heated under reflux for an hour, and then allowed to stand at room temperature for 5 hours. The solids thus formed were collected by filtration, washed with isopropylether, and then dried to give 100 mg of the titled compound (yield: 69%).

m.p.: 190°–200° C. (decomp.).

$^1$H-NMR(DMSO-d$_6$+TFA-d) δ: 8.61(1H, s), 4.5–3.84 (3H, m), 3.80–3.25 (4H, m), 3.20–2.85(1H, m), 2.77(3H, dd, J=3.12 Hz, J=1.41 Hz), 2.65–2.1(2H, m), 1.80–1.35(1H, m), 1.32–1.0(4H, m).

EXAMPLE 32

1-Cyclopropyl-7-([1α,5α,6β]-6-amino-3-azabicyclo[3.2.0]heptane-3-yl)-6,8-difluoro-1,4-dihydro-5-methyl-4-oxo-3-quinoline-carboxylic acid To a suspension of 200 mg of 1-cyclopropyl-1,4-dihydro-5-methyl-6,7,8-trifluoro-4-oxo-3-quinoline carboxylic acid in 5 ml of acetonitrile were added 153 mg of DBU and 230 mg of [1α,5α,6β]-6-amino-3-azabicyclo[3.2.0]heptane. The reaction mixture was heated under reflux at 100° C. for 6 hours. After cooling to room temperature, the resulting solution was concentrated under reduced pressure. To the residue was added 10 ml of distilled water. The resulting solution was neutralized with an aqueous 10% hydrochloric acid solution. The solids thus formed were collected by filtration, washed with a small amount of distilled water and then with isopropyl ether, and then dried to give 120 mg of the titled compound (yield: 46%).

m.p.: 260° C.

$^1$H-NMR(DMSO-d$_6$+TFA-d) δ8.67(1H, s), 8.5–7.7(2H, brs), 4.3–3.5(6H, m), 3.5–2.8(3H, m), 2.74(3H, d, J=3.2 Hz), 2.2–1.7(1H, m), 1.3–1.1(4H, m).

EXAMPLE 33

1-Cyclopropyl-7-([1α,5α,6β]-6-amino-3-azabicyclo[3.2.0]heptane-3-yl)-6,8-difluoro-1,4-dihydro-4-oxo-3-quinoline-carboxylic acid To a suspension of 200 mg of 1-cyclopropyl-1,4-dihydro-4-oxo-6,7,8-trifluoro-3-quinoline carboxylic acid in 6 ml of acetonitrile were added 160 mg of DBU and 240 mg of [1α,5α,6β]-6-amino-3-azabicyclo[3.2.0]heptane. The reaction mixture was heated under reflux at 80° C. for 10 hours, cooled to room temperature, and concentrated under reduced pressure. The residue was dissolved in 5 ml of distilled water. The resulting solution was neutralized with an aqueous 10% hydrochloric acid solution. The solids formed were collected by filtration under reduced pressure, washed with a small amount of distilled water and then with isopropyl alcohol, and then dried to give 160 mg of the titled compound (yield: 60%).

m.p.: 240° C.

$^1$H-NMR(DMSO-d$_6$+TFA-d) δ: 8.71(1H, s), 3.4–7.8(2H, brs), 7.86(1H, dd, J=2 Hz, 12 Hz), 4.4–3.4(6H, m), 3.4–2.6 (3H, m), 2.1–1.6(1H, m), 1.4–1.1(4H, m).

EXAMPLE 34

5-Amino-1-cyclopropyl-7-([1α,5α,6β]-6-amino-3-azabicyclo[3.2.0]heptane-3-yl)-6,8-difluoro-1,4-dihydro-4-oxo-3-quinoline-carboxylic acid, hydrochloride To a suspension of 180 mg of 5-amino-1-cyclopropyl-1,4-dihydro-4-oxo-6,7,8-trifluoro-3-quinoline-carboxylic acid in 2.2 ml of dimethyl sulfoxide was added 270 mg of [1α,5α,6β]-6-amino-3-azabicyclo[3.2.0]heptane. The reaction mixture was refluxed at 80° C. for 5 hours and then cooled to the room temperature. The residue was dissolved in 5 ml of distilled water. The resulting solution was adjusted to pH 1–2 with an aqueous 10% hydrochloric acid solution. The solids thus formed were collected by filtration and washed with isopropyl alcohol. The solids thus treated were added to and dissolved in 20 ml of methyl alcohol by heating. The resulting solution was placed in a refrigerator for 24 hours. The pale-yellow solids thus formed were collected by filtration under reduced pressure, washed with isopropyl alcohol, and then dried at 50° C. under reduced pressure to give 130 mg of the titled compound (yield: 50%).

m.p.: 243°–245° C. (decomp.).

$^1$H-NMR(DMSO-d$_6$+TFA-d) δ8.48(1H, s), 8.1(2H, brs), 4.3–3.3(7H, m), 3.2–2.7(3H, m), 1.2–0.9(4H, m).

EXAMPLE 35

1-Cyclopropyl-7-([1α,5α,6β]-6-hydroxy-3-azabicyclo[3.2.0]heptane-3-yl)-6-fluoro-1,4-dihydro-4-oxo-1,8-naphthyridine-3-carboxylic acid To a suspension of 200 mg of 7-chloro-1-cyclopropyl-1,4-dihydro-6-fluoro-4-oxo-1,8-naphthyridine-3-carboxylic acid in 5 ml of acetonitrile were added 150 mg of DBU and 260 mg of [1α,5α,6β]-6-hydroxy-3-azabicyclo[3.2.0]heptane. The reaction mixture was refluxed at 80° C. for 30 minutes and then concentrated under reduced pressure. After pouting 5 ml of distilled water, the resulting mixture was neutralized with an aqueous 5% hydrochloric acid solution. The solids thus formed were collected by filtration under reduced pressure and then dried to give 160 mg of the titled compound (yield: 63%).

m.p.: 243° C.

$^1$H-NMR(DMSO-d$_6$+TFA-d) δ: 8.57(1H, s), 7.96(1H, d, J=13.0 Hz), 4.7–4.05 (3H, m), 4.0–3.4(5H, m), 3.2–3.0(1H, m), 2.7–2.5 (2H, m), 1.2–1.0(4H, m).

EXAMPLE 36

1-Cyclopropyl-7-([1α,5α,6β]-6-amino-3-azabicyclo[3.2.0]heptane-3-yl)-6-fluoro-1,4-dihydro-4-oxo-1,8-naphthyridine-3-carboxylic acid To a suspension of 100 mg of 7-chloro-1-cyclopropyl-1,4-dihydro-6-fluoro-4-oxo-1,8-naphthyridine-3-carboxylic acid in 4 ml of acetonitrile were added 90 mg of DBU and 110 mg of [1α,5α,6β]-6-amino-3-azabicyclo[3.2.0]heptane. After refluxing at 80° C. for an hour, the reaction mixture was cooled to room temperature and allowed to stand overnight. The solids thus formed were collected by filtration, washed with isopropyl ether, and then dried to give 70 mg of the titled compound (yield: 55%).

m.p.: 242° C. (decomp.).

$^1$H-NMR(DMSO-d$_6$+TFA-d) δ: 8.60(1H, s), 8.2(2H, brs.), 8.00(1H, d, J=13.0 Hz), 4.6–2.9(8H, m), 2.6–2.4(1H, m), 2.0–1.8(1H, m), 1.2–0.95(4H, m).

EXAMPLE 37

7-([1α,5α,6β]-6-Amino-3-azabicyclo[3.2.0]heptane-3-yl)-1-(2,4-difluorophenyl)-1,4-dihydro-6-fluoro-4-oxo-1,8-naphthyridine-3-carboxylic acid To a suspension of 260 mg of 7-chloro-1-(2,4-difluorophenyl)-1,4-dihydro-6-fluoro-4-oxo-1,8-naphthyridine-3-carboxylic acid in 4 ml of acetonitrile were added 280 mg of DBU and 260 mg of [1α,5α,6β]-6-amino-1-methyl-3-azabicyclo[3.2.0]heptane. After refluxing at 80°

C. for 12 hours, the reaction mixture was cooled to room temperature and allowed to stand overnight. The solids thus formed were collected by filtration, washed with isopropyl ether, and then dried to give 156 mg of the titled compound (yield: 49.5%).

m.p.: 200° C.

$^1$H-NMR(DMSO-d$_6$+TFA-d) δ: 8.83(1H, s), 8.14(1H, d, J=13.0 Hz), 8.2–7.3 (3H, m), 4.5–2.7(8H, m), 2.4–1.6(1H, m).

EXAMPLE 38

7-([1α,5α,6β]-6-Amino-3-azabicyclo[3.2.0]heptane-3-yl)-1,4-dihydro-6-fluoro-1-(4-fluorophenyl)-4-oxo-1,8-naphthyridine-3-carboxylic acid To a suspension of 200 mg of 7-chloro-1,4-dihydro-6-fluoro-1-(4-fluorophenyl)-4-oxo-1,8-naphthyridine-3-carboxylic acid in 5 ml of acetonitrile were added 110 mg of DBU and 80 mg of [1α,5α,6β]-6-amino-3-azabicyclo[3.2.0] heptane. The reaction mixture was stirred at room temperature for 5 hours. The solvent, acetonitrile, was evaporated out under reduced pressure. The residue was dissolved in 2 ml of distilled water. The resulting solution was adjusted to pH 6–7 with an aqueous 10% hydrochloric acid solution, and allowed to stand overnight. The solids thus formed were collected by filtration, washed with a small amount of distilled water and then with isopropyl ether, and then dried to give 200 mg of the titled compound (yield: 82%).

m.p.: 275°–277° C. (decomp.).

$^1$H-NMR(DMSO-d$_6$+TFA-d) δ: 8.65(1H, s), 8.14(1H, d, J=12.8 Hz), 7.8–7.3 (4H, m), 4.3–1.5(9H, m).

EXAMPLE 39

7-([1α,5α,6β]-6-Amino-3-azabicyclo[3.2.0]heptane-3-yl)8-chloro-1-cyclopropyl-6-fluoro-1,4-dihydro-4-oxo-3-quinoline-carboxylic acid To a suspension of 200 mg of 8-chloro-1-cyclopropyl-6,7-difluoro-1,4-dihydro-4-oxo-3-quinoline-carboxylic acid in 3 ml of acetonitrile were added 140 mg of DBU and 100 mg of [1α,5α,6β]-6-amino-3-azabicyclo[3.2.0]heptane. The reaction mixture was refluxed at 80° C. for 6 hours and then cooled to room temperature. The solvent was evaporated out under reduced pressure. After pouring 3 ml of distilled water, the resulting mixture was neutralized with an aqueous 5% hydrochloric acid solution. The solids thus formed were filtered and added to 3 ml of ethyl alcohol. After dissolving the solids by heating, the resulting solution was placed in a refrigerator for 12 hours. The solids thus formed were collected by filtration under reduced pressure and washed with isopropyl alcohol. Drying the solids gave 80 mg of the titled compound (yield: 31%).

m.p.: 205°–207° C. (decomp.).

$^1$H-NMR(DMSO-d$_6$+TFA-d) δ: 9.20(1H, s), 8.2(1H, d, J=12.8 Hz), 4.8–4.2 (1H, m), 4.2–3.6(4H, m), 3.5–2.8(3H, m), 2.4–2.0(2H, m), 1.3–1.1(4H, m).

EXAMPLE 40

7-([1α,5α,6β]-6-Amino-3-azabicyclo[3.2.0]heptane-3-yl)-1-(2,4-difluorophenyl)-1,4-dihydro-6-fluoro-5-methyl-4-oxo-1,8-naphthyridine-3-carboxylic acid To a suspension of 130 mg of 7-chloro-1-(2,4-difluorophenyl)-1,4-dihydro-6-fluoro-5-methyl-4-oxo-1,8-naphthyridine-3-carboxylic acid in 4 ml of acetonitrile were added 70 mg of DBU and 80 mg of [1α,5α,6β]-6-amino-3-azabicyclo[3.2.0]heptane. The reaction mixture was stirred at 50° C. for 3 hours and then concentrated under reduced pressure. After pouring 2 ml of distilled water, the resulting solution was neutralized with an aqueous 5% hydrochloric acid solution. The solids thus formed were collected by filtration under reduced pressure, washed with a small amount of distilled water and then with isopropyl ether, and then dried to give 120 mg of the titled compound (yield: 77%).

m.p.: 130°–135° C. (decomp.).

$^1$H-NMR(DMSO-d$_6$+TFA-d) δ: 8.76(1H, s), 8.10(1H, d, J=12.8 Hz), 7.85–7.17 (3H, m), 4.2–4.0(1H, m), 3.8–3.3(4H, m), 3.2–2.9(2H, m), 2.75(3H, d, J=3.36 Hz), 2.35–2.0(1H, m), 1.75–1.5(1H, m).

EXAMPLE 41

(–)-7-([1α,5α,6β]-6-Amino-3-azabicyclo[3.2.0]heptane-3-yl)-1-(2,4-difluorophenyl)- 1,4-dihydro-6-fluoro-4-oxo-1,8-naphthyridine-3-carboxylic acid To a suspension of 180 mg of 7-chloro-1-(2,4-difluorophenyl)-1,4-dihydro-6-fluoro-4-oxo-1,8-naphthyridine-3-carboxylic acid in 5 ml of acetonitrile were added 100 mg of DBU and 80 mg of (–)-[1α,5α,6β]-6-amino-3-azabicyclo [3.2.0]heptane. The resulting mixture was stirred at 50° C. for 2 hours. The same procedure as in Example 37 was repeated to produce 80 mg of the titled compound (yield: 37%).

m.p.: 200° C.

$^1$H-NMR(DMSO-d$_6$+TFA-d) δ: 8.83(1H, s), 8.13(1H, d), 8.3–7.25(3H, m), 4.6–4.1(1H, m), 3.8–3.3(4H, m), 3.2–2.9 (2H, m), 2.4–2.0(1H, m), 1.6–1.4(1H, m).

EXAMPLE 42

7-([1α,5α,6β]-6-Amino-3-azabicyclo[3.2.0]heptane-3-yl)-1-(tert.-butyl)-6-fluoro-1,4-dihydro-4-oxo-1,8-naphthyridine-3-carboxylic acid To a suspension of 200 mg of 1-(tert.-butyl)-7-chloro-1,4-dihydro-6-fluoro-4-oxo-1,8-naphthyridine-3-carboxylic acid in 3 ml of acetonitrile were added 130 mg of DBU and [1α,5α,6β]-6-amino-3-azabicyclo[3.2.0]heptane. The resulting mixture was refluxed at 70° C. for an hour. The same procedure as in Example 39 was repeated to produce 100 mg of the titled compound (yield: 40%).

m.p.: 230°–233° C.

$^1$H-NMR(DMSO-d$_6$+TFA-d) δ: 8.86(1H, s), 8.02(1H, d, J=12.8 Hz), 4.3–4.15 (1H, m), 3.83–3.63(4H, m). 3.12–3.0 (2H, m), 2.54–2.25(2H, m), 1.89(9H, s).

EXAMPLE 43

(–)-7-([1α,5α,6β]-6-Amino-3-azabicyclo[3.2.0]heptane-3-yl)-1-cyclopropyl-1,4-dihydro-6-fluoro-5-methyl-1,8-naphthyridine-3-carboxylic acid To a suspension of 140 mg of 7-chloro-1-cyclopropyl-1,4-dihydro-6-fluoro-5-methyl; 1,8-naphthyridine-3-carboxylic acid in 4 ml of acetonitrile were added 100 mg of DBU and 80 mg of (–)-[1α,5α,6β]-6-6-amino-3-azabicyclo [3.2.0]heptane. The resulting mixture was stirred at room temperature for 24 hours. The same procedure as in Example 39 was repeated to produce 80 mg of the titled compound (yield: 45%).

m.p.: 140°–145° C.

$^1$H-NMR(DMSO-d$_6$+TFA-d) δ: 8.72(1H, s), 4.5–4.2(1H, m), 4.10–3.90 (1H, m), 3.7–3.3(4H, m), 2.75(3H, d, J=3.2 Hz), 2.7–2.4(2H, m), 1.9–1.6(2H, m), 1.3–1.1(4H, m).

EXAMPLE 44

7-([1α,5α,6β]-6-6-Amino-1-methyl-3-azabicyclo[3.2.0] heptane-3-yl)-1-cyclopropyl-6-fluoro-8-methoxy-1,4-dihydro-4-oxoquinoline-3-carboxylic acid 100 mg of 1-cyclopropyl-6,7-difluoro-8-methoxy-1,4-dihydro-4-oxo-quinoline-3-carboxylic acid and 120 mg of

[1α,5α,6β]-6-6-amino-1-methyl-3-azabicyclo[3.2.0] heptane were added to 2 ml of DMSO. The resulting mixture was heated at 80° to 90° C. for 2 hours. To the reaction solution was added 5 ml of water. The resulting solution was adjusted to pH 7 with an aqueous 5% hydrochloric acid solution and extracted twice with 30 ml of chloroform. The chloroform layer was removed and concentrated under reduced pressure. A small amount of water and ethanol was added to the residue. The resulting mixture was stirred at room temperature for an hour. The solids formed were collected by filtration, and then dried to give 20 mg of the titled compound as white solids (yield: 15%).

m.p.: 195°–200° C.

$^1$H-NMR(DMSO-d$_6$+TFA-d) δ: 8.73(1H, s), 7.77(1H, d, J=14.2 Hz), 4.3–1.9 (9H, m), 3.65(3H, s), 1.35(3H, s), 1.4–0.7 (4H, m).

EXAMPLE 45

7-([1α,5α,6β]-6-6-Amino-1-methyl-3-azabicyclo[3.2.0] heptane-3-yl)-1-cyclopropyl-6-fluoro-1,4-dihydro-4-oxo-1,8-naphthyridine-3-carboxylic acid To a suspension of 95 mg of 7-chloro-1-cyclopropyl-6-fluoro-1,4-dihydro-4-oxo-1,8-naphthyridine-3-carboxylic acid in 3 ml of acetonitrile were added 100 mg of DBU and 93 mg of [1α,5α,6β]-6-6-amino-1-methyl-3-azabicyclo [3.2.0]heptane. The reaction mixture stirred at room temperature for 3 hours and concentrated under reduced pressure. The residue was dissolved in water and neutralized with an aqueous 10% hydrochloric acid solution. The solids thus formed were collected by filtration, and then dried to give 98 mg of the titled compound as light-yellow solids (yield: 78%).

m.p.: 237°–240° C. (decomp.).

$^1$H-NMR(DMSO-d$_6$+TFA) δ: 8.52(1H, s), 7.94(1H, d, J=12.8 Hz), 4.3–3.4 (6H, m), 2.9–2.7(1H, m), 2.5–2.0(2H, m), 1.37(3H, s), 1.3–1.0(4H, m).

EXAMPLE 46

8-Chloro-1-cyclopropyl-6-fluoro-7-([1α,5α,6β]-6-1-methyl-6-methylamino-3-azabicyclo[3.2.0]heptane-3-yl)-1,4-dihydro-4-oxoquinoline-3-carboxylic acid To a suspension of 100 mg of 8-chloro-1-cyclopropyl-6,7-difluoro-1,4-dihydro-4-oxo-quinoline-3-carboxylic acid in 2 ml of acetonitrile were added 60 mg of DBU, and 60 mg of [1α,5α,6β]-6-1-methyl-6-methylamino-3-azabicyclo [3.2.0]heptane in 1 ml of acetonitrile. The reaction mixture was heated under reflux for 18 hours and concentrated under reduced pressure. The residue was dissolved in 3 ml of water, adjusted to pH 7 with an aqueous 5% hydrochloric acid solution, and allowed to stand overnight in a refrigerator. The solids thus formed were collected by filtration, washed with a small amount of water and ether, and then dried to give 30 mg of the titled compound as light-yellow solids (yield: 21%).

m.p.: 250°–255° C.

$^1$H-NMR(DMSO-d$_6$+TFA-d) δ: 8.87(1H, s), 7.94(1H, d, J=12.8 Hz), 4.6–4.2 (1H, m), 4.0–2.0(8H, m), 2.46(3H, s), 1.36(3H, m), 1.3–0.8(4H, m).

EXAMPLE 47

1-Cyclopropyl-6,8-difluoro-7-([1α,5α,6β]-6-1-methyl-6-methylamino-3-azabicyclo[3.2.0]heptane-3-yl)-1,4-dihydro-4-oxoquinoline-3-carboxylic acid To a suspension of 100 mg of 1-cyclopropyl-6,7,8-trifluoro-1,4-dihydro-4-oxoquinoline-3-carboxylic acid in 2 ml of acetonitrile were added 60 mg of DBU, and 60 mg of [1α,5α,6β]-6-1-methyl-6-methylamino-3-azabicyclo[3.2.0] heptane in 1 ml of acetonitrile. The reaction mixture was heated under reflux for 18 hours. The solids thus formed were collected by filtration, washed with a small amount of acetonitrile, and then dried to give 65 mg of the titled compound as white solids (yield: 46%).

m.p.: 260°–265° C. (decomp.).

$^1$H-NMR(DMSO-d$_6$+TFA) δ: 8.64(1H, s), 7.78(1H, dd, J=13.6 Hz, 1.84 Hz), 4.2–2.0 (9H, m), 2.50(3H, s), 1.32(3H, s), 1.3–0.9(4H, m).

EXAMPLE 48

1-Cyclopropyl-6-fluoro-7-([1α,5α,6β]-6-1-methyl-6-methylamino-3-azabicyclo-[3.2.0]heptane-3-yl)-1,4-dihydro,-4-oxo-1,8-naphthyridine-3-carboxylic acid To a suspension of 100 mg of 7-chloro-1-cyclopropyl-6-fluoro-1,4-dihydro-4-oxo-1,8-naphthyridine-3-carboxylic acid in 2 ml of acetonitrile were added 60 mg of DBU, and 60 mg of [1α,5α,6β]-6-1-methyl-6-methylamino-3-azabicyclo[3.2.0]heptane in 1 ml of acetonitrile. The reaction mixture was stirred at room temperature for 2 hours. The solids thus formed were collected by filtration, washed with a small amount of acetonitrile, and then dried to give 102 mg of the titled compound as white solids (yield: 74%).

m.p.: 245°–250° C. (decomp.).

$^1$H-NMR(DMSO-d$_6$+TFA) δ: 8.58(1H, s), 8.01(1H, d, J=12.8 Hz), 4.5–1.9 (9H, m), 2.49(3H, s), 1.37(3H, s), 1.3–0.9 (4H, m).

EXAMPLE 49

7-([1α,5α,6β]-6-6-Amino-3-azabicyclo[3.2.0]heptane-3-yl)-1-cyclopropyl-6-fluoro-1,4-dihydro-4-oxo-1,8-naphthyridine-3-carboxylic acid To a suspension of 140 mg of 7-chloro-1-cyclopropyl-6-fluoro-1,4-dihydro-4-oxo-1,8-naphthyridine-3-carboxylic acid in 5 ml of acetonitrile were added 140 mg of DBU and 70 mg of [1α,5α,6β]-6-6-amino-3-azabicyclo[3.2.0] heptane. The reaction mixture was at room temperature for 2 hours. The solids thus formed were collected by filtration, washed with a small amount of acetonitrile, and then recrystallized from ethanol to give 120 mg of the titled compound as white powder (yield: 68%).

m.p.: 225°–230° C.

$^1$H-NMR(DMSO-d$_6$+TFA-d) δ: 8.54(1H, s), 8.17(2H, brs), 7.95(1H, d, J=12.8 Hz), 4.5–1.8(10H, m), 1.2–1.0(4H, m).

EXAMPLE 50

7-([1α,5α,6β]-6-6-Amino-3-azabicyclo[3.2.0]heptane-3-yl)-1-cyclopropyl-6,8-difluoro-1,4-dihydro-1,4-oxoquinoline-3-carboxylic acid To a suspension of 100 mg of 1-cyclopropyl-6,7,8-trifluoro-1,4-dihydro-4-oxoquinoline-3-carboxylic acid in 4 ml of acetonitrile were added 60 mg of DBU and 60 mg of [1α,5α,6β]-6-6-amino-3-azabicyclo[3.2.0]heptane. After heating under reflux for 2 hours, the reaction mixture was cooled to room temperature and stirred for an hour. The solids thus formed were collected by filtration, washed with a small amount of acetonitrile, and then dried to give 90 mg of the titled compound as white solids (yield: 69%).

m.p.: 250° C. (decomp.).

$^1$H-NMR(DMSO-d$_6$+TFA-d) δ: 8.63(1H, s), 8.16(2H, brs), 7.75(1H, dd, J=12.8 Hz, 1.44 Hz), 4.3–1.8 (10H, m), 1.2–1.0(4H, m).

EXAMPLE 51

7-([1α,6α,8β]-6-8-Amino-3-azabicyclo[4.2.0]octane-3-yl)-1-cyclopropyl-6-fluoro-1,4-dihydro-4-oxo-1,8-naphthyridine-3-carboxylic acid, hydrochloride A mixture of 100 mg of 7-chloro-1-cyclopropyl-6-fluoro-1,4-dihydro-4-oxo-1,8-naphthyridine-3-carboxylic acid, 70 mg of [1α,6α,8β]-6-8-amino-3-azabicyclo[4.2.0]octane and 30 mg of DBU in 5 ml of acetonitrile was stirred at 40° C. for 3 hours. The solvents were evaporated off under reduced pressure, and 4 ml of ethanol was then added thereto. To the resulting solution, 4–5 drops of concentrated hydrochloric acid were added to dissolve the residue completely. The solids thus precipitated were filtered under reduced pressure, washed with ethanol, and then dried to give 100 mg of the titled compound (yield: 69%).

m.p.: 282°–284° C. (decomp.).

$^1$H-NMR(DMSO-$d_6$) δ: 8.59(1H, s), 8.02(1H, d, J=13.7 Hz), 4.90–3.10(6H, 3.10–1.40(4H, m).

EXAMPLE 52

7-([1α,6α,8β]-8-Amino-3-azabicyclo[4.2.0]octane-3-yl)-1-(2,4-phenyl)-1,4-dihydro-4-oxo-1,8-naphthyridine-3-carboxylic acid, hydrochloride The same procedure as in Example 51 was repeated using 100 mg of 7-chloro-1-(2,4-difluorophenyl)-6-fluoro-1,4-dihydro-4-oxo-1,8-naphthyridine-3-carboxylic acid, 30 mg of DBU and 70 mg of [1α,6α,8β]-8-amino-3-azabicyclo[4.2.0]octane to give 92 mg of the titled compound (yield: 74%).

m.p.: 267°–268° C.

$^1$H-NMR(DMSO-$d_6$) δ: 8.83(1H, s), 8.29(1H, d, J=13 Hz), 7.91–2.70(3H, m), 4.50–1.40(13H, m), 4.50–1.40(13H, m).

EXAMPLE 53

7-([1α,6α,8β]-8-Amino-3-azabicyclo[4.2.0]octane-3-yl)-1-(4-fluorophenyl)-1,4-dihydro-4-oxo-1,8-naphthyridine-3-carboxylic acid, hydrochloride The same procedure as in Example 51 was repeated using 100 mg of 7-chloro-1-(4-fluorophenyl)-1,4-dihydro-4-oxo-1,8-naphthyridine-3-carboxylic acid, 30 mg of DBU and 70 mg of [1α,6α,8β]-8-amino-3-azabicyclo[4.2.0]octane to give 108 mg of the titled compound (yield: 88%).

m.p.: 258°–260° C.

$^1$H-NMR(DMSO-$d_6$) δ: 11.17(1H, s), 10.89(2H, brs), 8.10(1H, d, J=13 Hz), 7.88–7.25(4H, m), 4.54–1.23(11H, m).

EXAMPLE 54

7-([1α,6α,8β]-8-Amino-3-azabicyclo[4.2.0]octane-3-yl)-1-cyclopropyl-6,8-difluoro-4-oxoquinoline-3-carboxylic acid A mixture of 100 mg of 1-cyclopropyl-6,7,8-trifluoro-1,4-dihydro-4-oxoquinoline-3-carboxylic acid and 60 mg of [1α,6α,8β]-8-amino-3-azabicyclo[4.2.0]octane in 3 ml of acetonitrile was heated under reflux with stirring for 4 hours and then cooled to room temperature. The solids precipitated were filtered and washed with acetonitrile. The impure solids obtained were suspended in 3 ml of water. This suspension was adjusted to pH 6–7 with a dilute hydrochloric acid solution to precipitate solids. After cooling in an ice bath, the solids were collected by filtration, washed with cold water and then with acetonitrile, and dried to give 100 mg of the titled compound (yield: 72%).

m.p.: 183°–185° C.

$^1$H-NMR(DMSO-$d_6$+TFA-d) δ: 8.68(1H, s), 8.00(2H, brs), 7.81(1H, dd, J=12 Hz, J=2 Hz), 4.08–1.40(11H, m), 1.10(4H, m).

EXAMPLE 55

7-([1α,6α,8β]-8-Amino-3-azabicyclo[4.2.0]octane-4-yl)-8-chloro-1-cyclopropyl-6-fluoro-1,4-dihydro-4-oxoquinoline-3-carboxylic acid The same procedure as in Example 54 was repeated using 100 mg of 8-chloro-1-cyclopropyl-6,7-difluoro-1,4-dihydro-4-oxoquinoline-3-carboxylic acid and 60 mg of [1α,6α,8β]-8-amino-4-azabicyclo[4.2.0]octane to give 86 mg of the titled compound (yield: 67%).

m.p.: 135°–137° C.

$^1$H-NMR(DMSO-$d_6$) δ: 8.8(1H, s), 7.9(1H, d, J=12.8 Hz), 4.3–1.5(14H, m), 1.5–0.9(4H, m).

EXAMPLE 56

7-([1α,6α,8β]-8-Amino-3-azabicyclo[4.2.0]octane-4-yl)-5-amino-1-cyclopropyl-6,8-difluoro-1,4-dihydro-4-oxoquinoline-3-carboxylic acid A suspension of 100 mg of 5-amino-1-cyclopropyl-6,7,8-trifluoro-1,4-dihydro- 4-oxoquinoline-3-carboxylic acid and 60 mg of [1α,6α,8β]-8-amino-3-azabicyclo[4.2.0]octane in 5 ml of acetonitrile was heated under reflux with stirring for 5 hours, and the volatile material was evaporated off under reduced pressure. To the residue, 5 ml of water was added. A small amount of an aqueous dilute sodium hydroxide solution was added to dissolve the residue completely. The solution was adjusted to pH 2–3 with an aqueous dilute hydrochloric acid solution. The solids thus precipitated were collected by filtration, washed with water, and then suspended in 5 ml of acetonitrile. Then, the solids were stirred for 30 minutes, collected by filtration, and then dried to give 75 mg of the titled compound (yield: 55%).

m.p.: 223°–226° C.

$^1$H-NMR(DMSO-$d_6$) δ: 8.77(1H, s), 4.2–1.3(12H, m), 1.3–0.8(4H, m).

EXAMPLE 57

7-([1α,6α,8β]-8-Amino-3-azabicyclo[4.2.0]octane-3-yl)-1-cyclopropyl-6-fluoro-1,4-dihydro-4-oxoquinoline-3-carboxylic acid The same procedure as in Example 56 was repeated using 100 mg of 1-cyclopropyl-6,7-difluoro-1,4-dihydro-4-oxoquinoline-3-carboxylic acid and 50 mg of [1α,6α,8β]-8-amino-3-azabicyclo[4.2.0]octane to give 104 mg of the titled compound (yield: 74%).

m.p.: 193°–195° C.

$^1$H-NMR(DMSO-$d_6$) δ8.6 (1H, s), 7.8(1H, d, J=14Hz), 7.5(1H, d, J=8.0 Hz), 3.95–1.50(14H, m), 1.5–0.9(4H, m).

EXAMPLE 58

7-([1α,6α,8β]-8-Amino-3-azabicyclo[4.2.0]octane-3-yl)-5-methyl-1-cyclopropyl-6,8-difluoro-1,4-dihydro-4-oxoquinoline-3-carboxylic acid A suspension of 100 mg of 5-methyl-1-cyclopropyl-6,7,8-trifluoro-4-oxoquinoline-3-carboxylic acid and 60 mg of [1α,6α,8β]-8-amino-3-azabicyclo[4.2.0]octane in 3 ml of acetonitrile was heated under reflux with stirring for an hour and then cooled to room temperature. The solids thus precipitated were filtered out and suspended in 3 ml of water. This suspension was adjusted to pH 11–12 with a small amount of a dilute sodium hydroxide solution to dissolve the solids completely. When the neutralization was completed, a trace amount of insoluble impurities were left. These impurities were filtered off. The filtrate was adjusted to pH 2–3 with a small amount of a dilute sodium hydroxide solution and cooled in an ice bath. The solids precipitated were collected by filtration, washed with cold water, and then dried to give 84 mg of the titled compound (yield: 62%).

m.p.: 232°–236° C.

$^1$H-NMR(DMSO-$d_6$) δ: 8.6(1H, s), 4.3–3.1(6H, m), 2.7 (3H, d, J=4 Hz), 2.6–1.4(6H, m), 1.3–0.9 (4H, m).

EXAMPLE 59

7-([1α,6α,8β]-8-Amino-3-azabicyclo[4.2.0.]octane-3-yl)-6-fluoro-1-tert.-butyl-1,4-dihydro-4-oxo-1,8-naphthyridine-3-carboxylic acid A suspension of 100 mg of 7-chloro-6-fluoro-1-tert.-butyl-1,4-dihydro-4-oxo-1,8-naphthyridine-3-carboxylic acid and 60 mg of [1α,6α,8β]-6-amino-3-azabicyclo[4.2.0]octane in 5 ml of acetonitrile was stirred under reflux for 30 minutes. The solution was cooled to room temperature. A small amount of solids precipitated were filtered out. The filtrate was concentrated under reduced pressure to 2 ml of acetonitrile. An aqueous dilute hydrochloric acid solution was added dropwise to the residue to neutralization. The solids thus precipitated were collected by filtration and then dried to give 93 mg of the titled compound (yield: 71%).

m.p.: 218°–223° C.

$^1$H-NMR(DMSO-d$_6$+TFA) δ: 8.90(1H, s), 8.09(1H, d, J=12.6 Hz), 4.80–2.35(11H, m 1.90(9H, s).

EXAMPLE 60

7-([1α,6α,8β]-8-Amino-3-azabicyclo[4.2.0]octane-3-yl)-8-chloro-6-fluoro-5-methyl-1-Cyclopropyl-1,4-dihydro-4-oxoquinoline-3-carboxylic acid A suspension of 100 mg of 8-chloro-6,7-difluoro-5-methyl-1-cyclopropyl-1,4-dihydro-4-oxoquinoline-3-carboxylic acid and 60 mg of [1 at, 6or, 813]-8-amino-3-azabicyclo-[4.2.0]octane in 3 ml of acetonitrile was heated under reflux with stirring for 4 hours, cooled to room temperature, washed with a small amount of cold acetonitrile, and then dried to give 55 mg of the titled compound as light-yellow solids (yield: 48%).

m.p.: 162°–166° C.

$^1$H-NMR(DMSO-d$_6$) δ: 8.78(1H, s), 4.60–2.90(5H, m), 2.70(3H, d, J=3.2 Hz), 2.30–1.40(6H, m), 0.85(4H, m).

EXAMPLE 61

7-([1α,6α,8β]-8-Amino-3-azabicyclo[4.2.0]octane-3-yl)-1-cyclopropyl-5-methyl-6-fluoro-1,4-dihydro-4-oxoquinoline-3-carboxylic acid A suspension of 100 mg of 1-cyclopropyl-5-methyl-6,7-difluoro-1,4-dihydro-4-oxo-quinoline- 3-carboxylic acid and 40 mg of [1α,6α,8β]-8-amino-3-azabicyclo[4.2.0]octane in 8 ml of acetonitrile was heated under reflux with stirring for 5 hours. After cooling to room temperature, the volatile solvent was evaporated off under reduced pressure. To the residue, 5 ml of water and a small amount of a dilute aqueous sodium hydroxide solution were added. A small amount of undissolved solids were filtered off. The filtrate was adjusted to pH 7 with a dilute hydrochloric acid solution. Sticky yellowish solids first precipitated were filtered off. Then, light-yellow solids precipitated were collected by filtration, washed with water, and then dried to give 64 mg of the titled compound (yield: 46%).

m.p.: 172°–175° C.

$^1$H-NMR(DMSO-d$_6$) δ: 8.54(1H, s), 7.38(1H, d, J=8 Hz), 4.40–3.09(5H, m), 2.75(3H, d, J=4 Hz), 2.40–1.45(6H, m), 0.40–0.90(4H, m).

EXAMPLE 62

(+)-7-([1α,6α,8β]-8-Amino-3-azabicyclo[4.2.0]octane-3-yl)-1-cyclopropyl-6-fluoro-1,4-dihydro-4-oxo-1,8-naphthyridine-3-carboxylic acid, hydrochloride The same procedure as in Example 51 was repeated using 100 mg of 7-chloro-1-cyclopropyl-6-fluoro-1,4-dihydro-4-oxo-1,8-naphthyridine-3-carboxylic acid, and 50 mg of (−)-[1α,6α,8β]-8-amino-3-azabicyclo[4.2.0]octane obtained in Preparation 19 to give 110 mg of the titled compound (yield: 76%).

m.p.: 285°–287° C.

$[α]_D^{20}$+50.6 (C=0.33, DMSO).

$^1$H-NMR(DMSO-d$_6$) δ: 8.59(1H, s), 8.02(1H, d, J=13.7 Hz), 4.90–7.10(6H, m), 3.10–1.40(6H, m), 1.40–0.80(4H, m).

EXAMPLE 63

(−)-7-([1α,6α,8β]-8-Amino-3-azabicyclo[4.2.0]octane-3-yl)-1-cyclopropyl-6-fluoro-1,4-dihydro-4-oxo-1,8-naphthyridine-3-carboxylic acid A suspension of 100 mg of 7-chloro-1-cyclopropyl-6-fluoro-1,4-dihydro-4-oxo-1,8-naphthyridine-3-carboxylic acid and 50 mg of (+)-[1α,6α,8β]-8-amino-3-azabicyclo[4.2.0]octane from Preparation 25 in 5 ml of acetonitrile was stirred at 40–50° C. for 3 hours. The resulting solution was cooled to room temperature, and thereto 3–4 drops of acetic acid were added. The resulting precipitates were filtered out and washed with cold acetonitrile. The solids thus formed were recrystallized twice from a mixture of chloroform and ethanol (3:2) to give 70 mg of the titled compound (yield: 53%).

m.p.: 204°–206° C.

$[α]_D^{20}$−38.8 (C=0.4, DMSO).

$^1$H-NMR(DMSO-d$_6$) δ: 8.51(1H, s), 7.98(1H, d, J=14.6 Hz), 6.80–5.80(2H, brs), 4.60–1.30(12H, m), 1.30–0.90 (4H, m).

EXAMPLE 64

(−)-7-([1α,6α,8β]-8-Amino-3-azabicyclo[4.2.0]octane-3-yl)-1-cyclopropyl-6,8-difluoro-1,4-dihydro-4-oxoquinoline-3-carboxylic acid To a suspension of 0.8 g of 1-cyclopropyl-6,7,8-trifluoro-1,4-dihydro-4-oxoquinoline-3-carboxylic acid, and 0.51 g of (−)-[1α,6α,8β]-8-amino-3-azabicyclo[4.2.0.]octane in 10 ml of acetonitrile, DBU was added dropwise to clear solution. The resulting solution was cooled to −20° C. The precipitates were collected by filtration and washed with cold acetonitrile. The solids thus obtained were recrystallized from a mixture of chloroform and ethanol (3:1) to give 0.78 g of the titled compound as nearly colorless solids (yield: 78%).

m.p.: 186°–190° C.

$[α]_D^{20}$−8.2 (C=1.0, CHCl$_3$).

$^1$H-NMR(DMSO-d$_6$+TFA) δ: 8.68(1H, s), 8.00(2H, brs), 7.81(1H, dd, J=12 Hz, J=2 Hz), 4.08–1.40(11H, m), 1.10 (4H, m).

EXAMPLE 65

(+)-7-([1α,6α,8β]-8-Amino-3-azabicyclo[4.2.0]octane-3-yl)-1-cyclopropyl-6,8-difluoro-4-oxoquinoline-3-carboxylic acid The same procedure as in Example 64 was repeated using 0.3 g of 1-cyclopropyl-6,7,8-trifluoro-1,4-dihydro-4-oxoquinoline-3-carboxylic acid and 0.21 g of (+)-[1α,6α, 8β]-8-amino-3-azabicyclo[4.2.0.]octane from Preparation 25 to give 0.32 g of the titled compound as white powder (yield: 78%).

m.p.: 186°–190° C.

$[α]_D^{20}$+9.8 (C=0.4, CHCl$_3$).

$^1$H-NMR(DMSO-d$_6$+TFA) δ: 8.68(1H, s), 8.00(2H, brs), 7.81(1H, dd, J=12 Hz, J=2 Hz), 4.08–1.40(11H, m), 1.10 (4H, m).

EXAMPLE 66

7-([1α,6α,8β]-8-Amino-3-azabicyclo[4.2.0]octane-3-yl)-1-cyclopropyl-6-fluoro-8-methoxy-1,4-dihydro-4-oxoquinoline-3-carboxylic acid To 3 ml of pyridine, 100 mg of 1-cyclopropyl-6,7-difluoro-8-methoxy-1,4-dihydro-4-oxoquinoline-3-carboxylic acid and 50 mg of [1α,6α,8β]-8-amino-3-azabicyclo-[4.2.0]octane were added. The resulting mixture was heated under reflux with stirring for 2 hours, and then cooled to room temperature. To the solution, 3–4 drops of water were added. After cooling in an ice bath with stirring, the solids precipitated were collected by filtration, washed with cold ethanol, and then dried to give 60 mg of the titled compound as white solids (yield: 44%).

m.p.: 186°–190° C.

$^1$H-NMR(DMSO-$d_6$+TFA) δ: 8.15(1H, s), 7.70(1H, d, J=12 Hz), 4.50–3.76 (6H, m), 3.70(3H, s), 3.57–1.28(6H, m), 1.09 (4H, m).

EXAMPLE 67

7-([1α,6α,8β]-8-Amino-6-methyl-3-azabicyclo[4.2.0]octane-3-yl)-1-cyclopropyl-6-fluoro-1,4-dihydro-4-oxo-1,8-naphthyridine-3-carboxylic acid, hydrochloride 150 mg of 7-chloro-1-cyclopropyl-6-fluoro-1,4-dihydro-4-oxo-1,8-naphthyridine-3-carboxylic acid and 190 mg of [1α,6α,8β]-8-amino-6-methyl-3-azabicyclo[4.2.0]octane were added to 3 ml of acetonitrile. The resulting mixture was stirred at 50° C. for 30 min. After cooling to room temperature, the resulting solution was added 3 drops of acetic acid and stirred for 10 minutes. The solids precipitated were filtered and washed with acetonitrile. The solids thus obtained were suspended in 3 ml of ethanol. To the suspension was added 4–5 drops of concentrated hydrochloric acid while stirring to dissolve any solids completely. The resulting solution was allowed to stand. The solids precipitated were collected by filtration, washed with cold ethanol and then with isopropyl ether. Drying the solids gave 150 mg of the titled compound (yield: 66%).

m.p.: 263°–266° C.

$^1$H-NMR(DMSO-$d_6$) δ: 15.37(1H, brs), 8.57(1H, s), 8.47 (1H, brs), 7.97 (1H, d, J=13.5 Hz), 4.60–2.60(6H, m), 2.65–1.57(5H, m), 1.48–0.93(7H, m).

EXAMPLE 68

7-([1α,6α,8β]-8-Amino-6-methyl-3-azabicyclo[4.2.0]octane-3-yl)-1-cyclopropyl-6-fluoro-1,4-dihydro-4-oxo-1,8-naphthyridine-3-carboxylic acid, hydrochloride The same procedure as in Example 67 was repeated using 150 mg of 7-chloro-1-cyclopropyl-6-fluoro-1,4-dihydro-4-oxo-1,8-naphthyridine-3-carboxylic acid and 190 mg of [1α,6α,8β]-8-amino-6-methyl-3-azabicyclo[4.2.0]octane to give 175 mg of the titled compound (yield: 77%).

m.p.: 252°–256° C.

$^1$H-NMR(DMSO-$d_6$) δ: 15.19(1H, brs), 8.57(1H, s), 7.99 (1H, d,J=13.4 Hz), 4.55–3.25(6H, m), 2.27–1.56(5H, m), 1.56–0.98(7H, m,).

EXAMPLE 69

7-([1α,6α,8β]-8-Amino-6-methyl-3-azabicyclo[4.2.0]octane-3-yl)-1-cyclopropyl-6,8-difluoro-1,4-dihydro-4-oxoquinoline-3-carboxylic acid The same procedure as in Example 14 was repeated using 100 mg of 1-cyclopropyl-6,7,8-trifluoro-1,4-dihydro-4-oxoquinoline-3-carboxylic acid and 120 mg of [1α,6α,8β]-8-amino-6-methyl-3-azabicyclo[4.2.0]octane to give 95 mg of the titled compound (yield: 72%).

m.p.: 265°–268° C.

$^1$H-NMR(DMSO-$d_6$+TFA) δ: 8.67(1H, s), 8.02(2H, brs), 7.81(1H, d, J=11.7 Hz), 4.25–2.90(6H, m), 2.36–1.50(5H, m), 1.50–0.97 (7H, m).

The titled compounds illustrated in the above Examples are summarized in Tables 1 and 2 below;

TABLE 1

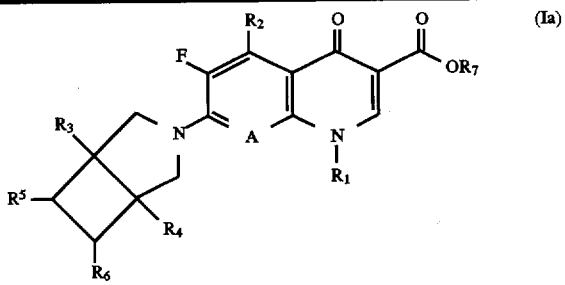

formula (Ia)

| Ex. No. | $R_1$ | $R_2$ | $R_3$ | $R_4$ | $R_5$ | $R_6$ | A | Remark |
|---|---|---|---|---|---|---|---|---|
| 1 | cyclopropyl | H | $CH_3$ | H | H | $NH_2$ | C—H | |
| 2 | cyclopropyl | H | $CH_3$ | H | H | $NH_2$ | C—F | |
| 3 | cyclopropyl | $NH_2$ | $CH_3$ | H | H | $NH_2$ | C—F | |
| 4 | 2,4-difluorophenyl | H | $CH_3$ | H | H | $NH_2$ | C—F | |
| 5 | cyclopropyl | $CH_3$ | $CH_3$ | H | H | $NH_2$ | C—F | |
| 6 | cyclopropyl | H | $CH_3$ | H | H | $NH_2$ | C—Cl | |
| 7 | cyclopropyl | H | $CH_3$ | H | H | $NH_2$ | N | |
| 8 | 2,4-difluorophenyl | H | $CH_3$ | H | H | $NH_2$ | N | |
| 9 | 4-fluorophenyl | H | $CH_3$ | H | H | $NH_2$ | N | |
| 10 | t-butyl | H | $CH_3$ | H | H | $NH_2$ | N | |
| 11 | 2,4-difluorophenyl | $CH_3$ | $CH_3$ | H | H | $NH_2$ | N | |
| 12 | cyclopropyl | H | $CH_3$ | H | H | $NH_2$ | N | (+) |
| 13 | cyclopropyl | H | $CH_3$ | H | H | $NH_2$ | C—F | (−) |
| 14 | cyclopropyl | H | $CH_3$ | H | H | $NH_2$ | C—F | (+) |
| 15 | cyclopropyl | H | $CH_3$ | H | H | OH | C—F | |
| 16 | cyclopropyl | H | $CH_3$ | H | H | OH | N | |
| 17 | cyclopropyl | $CH_3$ | $CH_3$ | H | H | $NH_2$ | C—F | (−) |

TABLE 1-continued formula (Ia)

| Ex. No. | R₁ | R₂ | R₃ | R₄ | R₅ | R₆ | A | Remark |
|---|---|---|---|---|---|---|---|---|
| 18 | cyclopropyl | NH₂ | CH₃ | H | H | NH₂ | C—F | (−) |
| 19 | t-butyl | H | CH₃ | H | H | NH₂ | N | (−) |
| 20 | cyclopropyl | H | CH₃ | H | H | NH₂ | C—Cl | (−) |
| 21 | 2,4-difluorophenyl | H | CH₃ | H | H | NH₂ | N | (−) |
| 22 | 4-fluorophenyl | H | CH₃ | H | H | NH₂ | N | (−) |
| 23 | cyclopropyl | H | H | CH₃ | H | NH₂ | C—F | |
| 24 | 4-fluorophenyl | H | H | H | H | NH₂ | N | |
| 25 | cyclopropyl | H | H | CH₃ | H | NH₂ | C—Cl | |
| 26 | cyclopropyl | H | H | CH₃ | H | NH₂ | N | |
| 27 | 2,4-difluorophenyl | H | H | CH₃ | H | NH₂ | N | |
| 28 | 2,4-difluorophenyl | CH₃ | CH₃ | H | H | NH₂ | N | (−) |
| 29 | cyclopropyl | H | H | H | H | OH | C—F | |
| 30 | cyclopropyl | NH₂ | H | H | H | OH | C—F | |
| 31 | cyclopropyl | CH₃ | H | H | H | OH | C—F | |
| 32 | cyclopropyl | CH₃ | H | H | H | NH₂ | C—F | |
| 33 | cyclopropyl | H | H | H | H | NH₂ | C—F | |
| 34 | cyclopropyl | NH₂ | H | H | H | NH₂ | C—F | |
| 35 | cyclopropyl | H | H | H | H | OH | N | |
| 36 | cyclopropyl | H | H | H | H | NH₂ | N | |
| 37 | 2,4-difluorophenyl | H | H | H | H | NH₂ | N | |
| 38 | 4-fluorophenyl | H | H | H | H | NH₂ | N | |
| 39 | cyclopropyl | H | H | H | H | NH₂ | N | |
| 40 | 2,4-difluorophenyl | CH₃ | H | H | H | NH₂ | N | |
| 41 | 2,4-difluorophenyl | H | H | H | H | NH₂ | N | (−) |
| 42 | t-butyl | H | H | H | H | NH₂ | N | |
| 43 | cyclopropyl | CH₃ | H | H | H | NH₂ | N | (−) |
| 44 | cyclopropyl | H | CH₃ | H | H | NH₂ | C—OCH₃ | |
| 45 | cyclopropyl | H | CH₃ | H | H | NH₂ | N | |
| 46 | cyclopropyl | H | CH₃ | H | H | NHCH₃ | C—Cl | |
| 47 | cyclopropyl | H | CH₃ | H | H | NHCH₃ | C—F | |
| 48 | cyclopropyl | H | CH₃ | H | H | NHCH₃ | N | |
| 49 | cyclopropyl | H | H | H | H | NH₂ | N | |
| 50 | cyclopropyl | H | H | H | H | NH₂ | C—F | |

TABLE 2 formula (Ib)

| Ex. No. | R₁ | R₂ | R₃ | R₄ | R₅ | R₆ | A | Remark |
|---|---|---|---|---|---|---|---|---|
| 51 | cyclopropyl | H | H | H | H | NH₂ | N | |
| 52 | 2,4-difluorophenyl | H | H | H | H | NH₂ | N | |
| 53 | 4-fluorophenyl | H | H | H | H | NH₂ | N | |
| 54 | cyclopropyl | H | H | H | H | NH₂ | C—F | |
| 55 | cyclopropyl | H | H | H | H | NH₂ | C—Cl | |
| 56 | cyclopropyl | NH₂ | H | H | H | NH₂ | C—F | |

TABLE 2-continued formula (Ib)

| Ex. No. | R₁ | R₂ | R₃ | R₄ | R₅ | R₆ | A | Remark |
|---|---|---|---|---|---|---|---|---|
| 57 | cyclopropyl | H | H | H | H | NH₂ | C—H | |
| 58 | cyclopropyl | CH₃ | H | H | H | NH₂ | C—F | |
| 59 | t-butyl | H | H | H | H | NH₂ | N | |
| 60 | cyclopropyl | CH₃ | H | H | H | NH₂ | C—Cl | |
| 61 | cyclopropyl | CH₃ | H | H | H | NH₂ | C—H | |
| 62 | cyclopropyl | H | H | H | H | NH₂ | N | (+) |
| 63 | cyclopropyl | H | H | H | H | NH₂ | N | (−) |
| 64 | cyclopropyl | H | H | H | H | NH₂ | C—F | (−) |
| 65 | cyclopropyl | H | H | H | H | NH₂ | C—F | (+) |
| 66 | cyclopropyl | H | H | H | H | NH₂ | C—OCH₃ | |
| 67 | cyclopropyl | H | CH₃ | H | H | NH₂ | N | |
| 68 | cyclopropyl | H | CH₃ | H | H | NH₂ | N | |
| 69 | cyclopropyl | H | CH₃ | H | H | NH₂ | C—F | |

In Vitro Antibacterial Activity

In order to demonstrate antibacterial activity of the pyridone carboxylic acid derivatives of the present invention, the minimum inhibitory concentrations (MICs, μg/ml) of several compounds synthesized in the examples were determined in accordance with the method described in *Chemotherapy*, 29 (1), p.76 (1981). The selected compounds for this test were those of Examples 12, 18, 20, 21, 31, 39, 41, 55, 56, 62 and 64. Ofloxacin(OFLX) and Ciprofloxacin (CPFX) were used as reference compounds.

The results are shown in Table 3 below.

TABLE 3

| TESTED STRAIN | COMPOUND OF EXAMPLE | | | | | | | | | | | | |
|---|---|---|---|---|---|---|---|---|---|---|---|---|---|
| | 12 | 18 | 20 | 21 | 31 | 39 | 41 | 55 | 56 | 62 | 64 | OFLX | CPFX |
| A | 0.1 | <0.001 | <0.001 | 0.013 | 0.2 | 0.025 | 0.05 | 0.007 | 0.004 | 0.05 | 0.03 | 0.39 | 0.2 |
| B | 0.39 | 0.2 | 0.1 | 0.1 | 0.78 | 0.20 | 1.56 | 0.013 | 0.025 | 0.05 | 0.012 | 1.56 | 3.13 |
| C | 0.05 | <0.001 | <0.001 | 0.025 | 0.2 | 0.025 | 0.05 | 0.007 | 0.004 | 0.05 | 0.003 | 0.39 | 0.78 |
| D | 0.025 | <0.001 | <0.001 | 0.004 | 0.002 | 0.007 | 0.007 | 0.013 | 0.004 | 0.05 | 0.003 | 0.05 | 0.007 |
| E | 0.004 | <0.001 | <0.001 | <0.001 | <0.001 | <0.001 | <0.001 | 0.004 | 0.2 | 0.007 | <0.001 | 0.013 | <0.001 |
| F | 0.156 | 1.56 | 0.78 | 0.78 | 3.13 | 1.56 | 1.56 | 3.13 | 3.13 | 3.13 | 3.13 | 3.13 | 0.39 |

NOTE;
*A: *Staphylococcus aureus* smith
B: *Streptococcus pyogen*
C: Methicilline Resistant *Staphylococcus aureus* C2208
D: *Escherichia coli* A10536
E: *Klebsiella pneumonia* A10031
F: *Pseudomonas aeruginosa* A27853

What is claimed is:
1. A compound of the formula:

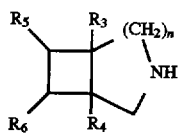

wherein n is 1 or 2; $R_3$ and $R_4$ each represent a hydrogen atom or a lower alkyl group; and $R_5$ and $R_6$ each represent a hydrogen atom, a hydroxy or an amino group which is unsubstituted or substituted by a lower alkyl group, with a proviso that one of $R_5$ and $R_6$ is not a hydrogen atom, and that at least one of $R_3$ and $R_4$ is a hydrogen atom.

2. An azabicyclic compound selected from the group consisting of 6-amino-1-methyl-3-azabicyclo[3,2,0]heptane; [1α,5α,6β]-6-hydroxy-1-methyl-3-azabicyclo[3,2,0]heptane; and [1α,6α,8β]-8-amino-3-azabicyclo[4,2,0]octane.

3. The compound according to claim 2, wherein the compound is 6-amino-1-methyl-3-azabicyclo[3.2.0]heptane.

4. The compound according to claim 2, wherein the compound is [1α,5α,6β]-6-hydroxy-1-methyl-3-azabicyclo[3.2.0]heptane.

5. The compound according to claim 1, wherein the compound is 6-amino-1-methyl-3-azabicyclo[3.2.0]heptane.

6. The compound according to claim 1, wherein the compound is [1α,5α,6β]-6-hydroxy-1-methyl-3-azabicyclo[3.2.0]heptane.

7. The compound according to claim 1, wherein the compound is [1α,6α,8β]-8-amino-3-azabicyclo [4.2.0]octane.

8. A process for preparing a compound according to claim 1, comprising
   condensing N-p-toluenesulfonyl-1-methyl-6-oxo-3-azabicyclo[3.2.0]heptane or N-p-toluenesulfonyl-8-oxo-3-azabicyclo[4.2.0]octane with methoxyamine or hydroxyamine hydrochloride in the presence of a base to produce a methoxyimine or hydroxyimine compound;
   reducing said methoxyimine or hydroxyimine compound with a reducing agent to produce an amino compound; and
   deprotecting said amino compound in the presence of an acid.

9. A process for preparing a compound according to claim 1, comprising
   condensing N-p-toluenesulfonyl-1-methyl-6-oxo-3-azabicyclo[3.2.0]heptane or N-p-toluenesulfonyl-8-oxo-3-azabicyclo[4.2.0]octane with methoxyamine or hydroxyamine hydrochloride in the presence of a base to produce a methoxyimine or hydroxyimine compound;
   reducing said methoxyimine or hydroxyimine compound with a reducing agent to produce an amino compound;
   condensing said amino compound with N-p-toluenesulphonyl-L-phenylalanine to produce an amide compound in racemic form;
   resolving said amide compound through column chromatography or recrystallization into each of optically active diastereomers thereof; and
   hydrolyzing said diastereomer with an acid to give an optical isomer.

10. A process for preparing a compound according to claim 1, comprising reducing N-p-toluenesulfonyl-1-methyl-6-oxo-3-azabicyclo[3.2.0]heptane with a reducing agent to produce an alcoholic compound; and
    deprotecting said alcoholic compound in the presence of an acid.

11. The compound according to claim 3, wherein the compound is [1α,6α,8β]-8-amino-3-azabicyclo[4.2.0]octane.

* * * * *